US011246639B2

(12) United States Patent
Rajagopalan et al.

(10) Patent No.: US 11,246,639 B2
(45) Date of Patent: Feb. 15, 2022

(54) METHODS, SYSTEMS AND DEVICES FOR PERFORMING MULTIPLE TREATMENTS ON A PATIENT

(71) Applicant: Fractyl Laboratories, Inc., Waltham, MA (US)

(72) Inventors: Harith Rajagopalan, Wellesley Hills, MA (US); Jay Caplan, Belmont, MA (US); J. Christopher Flaherty, Auburndale, FL (US)

(73) Assignee: Fractyl Health, Inc., Lexington, MA (US)

( * ) Notice: Subject to any disclaimer, the term of this patent is extended or adjusted under 35 U.S.C. 154(b) by 0 days.

(21) Appl. No.: 14/673,565

(22) Filed: Mar. 30, 2015

(65) Prior Publication Data

US 2016/0008050 A1 Jan. 14, 2016

Related U.S. Application Data

(63) Continuation of application No. PCT/US2013/063753, filed on Oct. 7, 2013.
(Continued)

(51) Int. Cl.
*A61B 18/04* (2006.01)
*A61B 17/3203* (2006.01)
(Continued)

(52) U.S. Cl.
CPC .......... *A61B 18/04* (2013.01); *A61B 17/3203* (2013.01); *A61B 18/08* (2013.01);
(Continued)

(58) Field of Classification Search
CPC ........ A61F 5/0036–0066; A61F 5/0073; A61F 5/0076; A61N 1/36007;
(Continued)

(56) References Cited

U.S. PATENT DOCUMENTS 5,084,044 A 1/1992 Quint
5,190,540 A 3/1993 Lee
(Continued)

FOREIGN PATENT DOCUMENTS

CA 2666661 C 1/2015
CN 1771888 A 5/2006
(Continued)

OTHER PUBLICATIONS

Tolman et al, Spectrum of Liver Disease in Type 2 Diabetes and Management of Patients With Diabetes and Liver Disease, Mar. 2007, Diabetes Care, vol. 30, No. 3, pp. 734-743 (Year: 2007).*
(Continued)

*Primary Examiner* — William H Matthews
(74) *Attorney, Agent, or Firm* — Wilson Sonsini Goodrich & Rosati

(57) ABSTRACT

Methods, systems and devices for treating a patient include performing a first treatment to treat a first portion of tissue and performing a second treatment to treat a second portion of tissue. The second portion of tissue is treated at least twenty-four hours after the first portion of tissue is treated. In particular embodiments, the first portion of tissue includes duodenal tissue, and the second portion of tissue includes duodenal or other gastrointestinal tissue.

26 Claims, 4 Drawing Sheets

Related U.S. Application Data

(60) Provisional application No. 61/710,318, filed on Oct. 5, 2012.

(51) Int. Cl.
  *A61B 18/14* (2006.01)
  *A61B 18/08* (2006.01)
  *A61N 1/36* (2006.01)
  A61B 18/00 (2006.01)
  A61B 5/00 (2006.01)
  A61B 5/145 (2006.01)
  A61B 18/02 (2006.01)

(52) U.S. Cl.
  CPC .......... *A61B 18/14* (2013.01); *A61B 18/1492* (2013.01); *A61N 1/36007* (2013.01); A61B 5/14546 (2013.01); A61B 5/42 (2013.01); A61B 18/02 (2013.01); A61B 2018/00482 (2013.01); A61B 2018/00494 (2013.01); A61B 2018/00577 (2013.01); A61B 2018/046 (2013.01)

(58) Field of Classification Search
  CPC ........... A61B 2017/00818; A61B 2018/00482; A61B 2018/00494; A61B 2018/00577; A61B 18/04; A61B 18/08; A61B 18/28
  See application file for complete search history.

(56) References Cited

U.S. PATENT DOCUMENTS

| | | | |
|---|---|---|---|
| 5,423,754 A | 6/1995 | Cornelius et al. | |
| 5,471,982 A | 12/1995 | Edwards et al. | |
| 5,496,311 A | 3/1996 | Abele et al. | |
| 5,515,100 A | 5/1996 | Nogo | |
| 5,542,928 A | 8/1996 | Evans et al. | |
| 5,549,559 A | 8/1996 | Eshel | |
| 5,575,772 A | 11/1996 | Lennox | |
| 5,704,934 A | 1/1998 | Neuwirth et al. | |
| 5,730,719 A | 3/1998 | Edwards | |
| 5,800,484 A | 9/1998 | Gough et al. | |
| 5,827,269 A | 10/1998 | Saadat | |
| 5,859,037 A | 1/1999 | Whitcomb et al. | |
| 5,869,037 A | 2/1999 | Crystal et al. | |
| 5,871,525 A | 2/1999 | Edwards et al. | |
| 5,879,347 A | 3/1999 | Saadat | |
| 5,957,962 A | 9/1999 | Wallsten et al. | |
| 5,964,753 A | 10/1999 | Edwards | |
| 6,009,877 A | 1/2000 | Edwards | |
| 6,053,937 A | 4/2000 | Edwards et al. | |
| 6,056,744 A | 5/2000 | Edwards | |
| 6,066,132 A | 5/2000 | Chen et al. | |
| 6,077,257 A | 6/2000 | Edwards et al. | |
| 6,112,123 A | 8/2000 | Kelleher et al. | |
| 6,293,909 B1 | 9/2001 | Chu et al. | |
| 6,325,777 B1 | 12/2001 | Zadno-Azizi et al. | |
| 6,325,798 B1 | 12/2001 | Edwards et al. | |
| 6,338,726 B1 | 1/2002 | Edwards et al. | |
| 6,358,245 B1 | 3/2002 | Edwards et al. | |
| 6,402,744 B2 | 6/2002 | Edwards et al. | |
| 6,405,732 B1 | 6/2002 | Edwards et al. | |
| 6,409,723 B1 | 6/2002 | Edwards | |
| 6,425,887 B1 | 7/2002 | McGuckin et al. | |
| 6,443,947 B1 | 9/2002 | Marko et al. | |
| 6,544,226 B1 | 4/2003 | Gaiser et al. | |
| 6,673,070 B2 | 1/2004 | Edwards et al. | |
| 6,712,814 B2 | 3/2004 | Edwards et al. | |
| 6,802,841 B2 | 10/2004 | Utley et al. | |
| 6,905,496 B1 | 6/2005 | Ellman et al. | |
| 6,962,587 B2 | 11/2005 | Johnson et al. | |
| 6,974,456 B2 | 12/2005 | Edwards et al. | |
| 7,077,841 B2 | 7/2006 | Gaiser et al. | |
| 7,111,627 B2 | 9/2006 | Stack et al. | |
| 7,122,031 B2 | 10/2006 | Edwards et al. | |
| 7,125,407 B2 | 10/2006 | Edwards et al. | |
| 7,156,860 B2 | 1/2007 | Wallsten | |
| 7,165,551 B2 | 1/2007 | Edwards et al. | |
| 7,241,295 B2 | 7/2007 | Maguire | |
| 7,326,207 B2 | 2/2008 | Edwards | |
| 7,371,215 B2 | 5/2008 | Colliou et al. | |
| 7,387,626 B2 | 6/2008 | Edwards et al. | |
| 7,422,587 B2 | 9/2008 | Bek et al. | |
| 7,507,234 B2 | 3/2009 | Utley et al. | |
| 7,507,238 B2 | 3/2009 | Edwards et al. | |
| 7,530,979 B2 | 5/2009 | Ganz et al. | |
| 7,556,628 B2 | 7/2009 | Utley et al. | |
| 7,585,296 B2 | 9/2009 | Edwards et al. | |
| 7,632,268 B2 | 12/2009 | Edwards et al. | |
| 7,632,291 B2 | 12/2009 | Stephens et al. | |
| 7,648,500 B2 | 1/2010 | Edwards et al. | |
| 7,758,623 B2 | 7/2010 | Dzeng et al. | |
| 7,762,977 B2 | 7/2010 | Porter et al. | |
| 7,947,038 B2 | 5/2011 | Edwards | |
| 7,959,627 B2 | 6/2011 | Utley et al. | |
| 7,993,336 B2 | 8/2011 | Jackson et al. | |
| 7,997,278 B2 | 8/2011 | Utley et al. | |
| 8,012,149 B2 | 9/2011 | Jackson et al. | |
| 8,066,689 B2 | 11/2011 | Mitelberg et al. | |
| 8,152,803 B2 | 4/2012 | Edwards et al. | |
| 8,177,853 B2 | 5/2012 | Stack et al. | |
| 8,192,426 B2 | 6/2012 | Stern et al. | |
| 8,251,992 B2 | 8/2012 | Utley et al. | |
| 8,273,012 B2 | 9/2012 | Wallace et al. | |
| 8,323,229 B2 | 12/2012 | Shin et al. | |
| 8,364,237 B2 | 1/2013 | Stone et al. | |
| 8,377,055 B2 | 2/2013 | Jackson et al. | |
| 8,641,711 B2 | 2/2014 | Kelly et al. | |
| 8,740,894 B2 | 6/2014 | Edwards | |
| 8,790,705 B2 | 7/2014 | Geigle et al. | |
| 9,364,283 B2 | 6/2016 | Utley et al. | |
| 9,555,020 B2 | 1/2017 | Pasricha | |
| 9,615,880 B2 | 4/2017 | Gittard et al. | |
| 9,757,535 B2 | 9/2017 | Rajagopalan et al. | |
| 9,844,641 B2 | 12/2017 | Rajagopalan et al. | |
| 10,610,663 B2 | 4/2020 | Rajagopalan et al. | |
| 10,765,474 B2 | 9/2020 | Kadamus et al. | |
| 10,864,352 B2 | 12/2020 | Rajagopalan et al. | |
| 10,869,718 B2 | 12/2020 | Rajagopalan et al. | |
| 2002/0013581 A1 | 1/2002 | Edwards et al. | |
| 2002/0077594 A1 | 6/2002 | Chien et al. | |
| 2002/0115992 A1 | 8/2002 | Utley et al. | |
| 2002/0192162 A1 | 12/2002 | Green | |
| 2003/0040804 A1 | 2/2003 | Stack et al. | |
| 2003/0093072 A1 | 5/2003 | Friedman | |
| 2003/0153905 A1 | 8/2003 | Edwards et al. | |
| 2003/0233065 A1 | 12/2003 | Steward et al. | |
| 2004/0082859 A1 | 4/2004 | Schaer | |
| 2004/0087936 A1 | 5/2004 | Stern et al. | |
| 2004/0133256 A1 | 7/2004 | Callister | |
| 2004/0148034 A1 | 7/2004 | Kagan et al. | |
| 2004/0204768 A1* | 10/2004 | Geitz | A61F 2/04 623/23.65 |
| 2004/0215180 A1 | 10/2004 | Starkebaum et al. | |
| 2004/0215296 A1 | 10/2004 | Ganz et al. | |
| 2004/0220559 A1 | 11/2004 | Kramer et al. | |
| 2005/0096638 A1 | 5/2005 | Starkebaum et al. | |
| 2005/0154386 A1 | 7/2005 | West et al. | |
| 2005/0165437 A1 | 7/2005 | Takimoto | |
| 2005/0171524 A1 | 8/2005 | Stern et al. | |
| 2005/0192652 A1 | 9/2005 | Cioanta et al. | |
| 2005/0203489 A1 | 9/2005 | Saadat et al. | |
| 2005/0222558 A1 | 10/2005 | Baxter et al. | |
| 2005/0245943 A1 | 11/2005 | Zvuloni et al. | |
| 2005/0251116 A1 | 11/2005 | Steinke et al. | |
| 2005/0273090 A1 | 12/2005 | Nieman et al. | |
| 2006/0070631 A1 | 4/2006 | Scopton et al. | |
| 2006/0118127 A1 | 6/2006 | Chinn | |
| 2006/0135963 A1 | 6/2006 | Kick et al. | |
| 2006/0155261 A1 | 7/2006 | Bek et al. | |
| 2006/0205992 A1 | 9/2006 | Lubock et al. | |
| 2006/0247683 A1 | 11/2006 | Danek et al. | |
| 2006/0259030 A1 | 11/2006 | Utley et al. | |
| 2006/0293742 A1 | 12/2006 | Dann et al. | |

(56) References Cited

U.S. PATENT DOCUMENTS

| | | |
|---|---|---|
| 2007/0016262 A1 | 1/2007 | Gross et al. |
| 2007/0032788 A1 | 2/2007 | Edwards et al. |
| 2007/0100355 A1 | 5/2007 | Bonde et al. |
| 2008/0045785 A1 | 2/2008 | Oyatsu |
| 2008/0107744 A1 | 5/2008 | Chu |
| 2008/0119788 A1 | 5/2008 | Winter |
| 2008/0125760 A1 | 5/2008 | Gilboa |
| 2008/0125803 A1 | 5/2008 | Sadamasa et al. |
| 2008/0147056 A1 | 6/2008 | Van Der Weide et al. |
| 2008/0207994 A1 | 8/2008 | Gonon |
| 2008/0243112 A1 | 10/2008 | De Neve |
| 2008/0275445 A1 | 11/2008 | Kelly et al. |
| 2008/0319504 A1 | 12/2008 | Loushin et al. |
| 2009/0012469 A1 | 1/2009 | Nita |
| 2009/0012512 A1 | 1/2009 | Utley et al. |
| 2009/0012518 A1 | 1/2009 | Utley et al. |
| 2009/0018533 A1 | 1/2009 | Perkins et al. |
| 2009/0018604 A1 | 1/2009 | Mitelberg et al. |
| 2009/0048593 A1 | 2/2009 | Ganz et al. |
| 2009/0069805 A1 | 3/2009 | Fischer et al. |
| 2009/0270851 A1 | 10/2009 | Babkin et al. |
| 2010/0022891 A1 | 1/2010 | Zuluaga et al. |
| 2010/0030190 A1 | 2/2010 | Singh |
| 2010/0114087 A1 | 5/2010 | Edwards et al. |
| 2010/0114325 A1 | 5/2010 | Yang et al. |
| 2010/0168561 A1 | 7/2010 | Anderson |
| 2010/0168624 A1 | 7/2010 | Sliwa |
| 2010/0204673 A1 | 8/2010 | Miller |
| 2010/0204688 A1 | 8/2010 | Hoey et al. |
| 2010/0217151 A1 | 8/2010 | Gostout et al. |
| 2010/0234840 A1 | 9/2010 | Jackson et al. |
| 2010/0256775 A1 | 10/2010 | Belhe et al. |
| 2010/0260703 A1 | 10/2010 | Yankelson et al. |
| 2011/0046537 A1 | 2/2011 | Errico et al. |
| 2011/0091564 A1 | 4/2011 | Chu |
| 2011/0106273 A1 | 5/2011 | Belhe et al. |
| 2011/0160648 A1 | 6/2011 | Hoey |
| 2011/0172659 A1 | 7/2011 | Brannan |
| 2011/0184401 A1 | 7/2011 | Iwata et al. |
| 2011/0319809 A1 | 12/2011 | Smith |
| 2012/0004654 A1 | 1/2012 | Jackson et al. |
| 2012/0016364 A1 | 1/2012 | Mayse et al. |
| 2012/0059364 A1 | 3/2012 | Baust et al. |
| 2012/0197245 A1 | 8/2012 | Burnett et al. |
| 2012/0271277 A1 | 10/2012 | Fischell et al. |
| 2012/0271301 A1 | 10/2012 | Fischell et al. |
| 2012/0289952 A1 | 11/2012 | Utley et al. |
| 2013/0071466 A1 | 3/2013 | Chancellor et al. |
| 2013/0178910 A1 | 7/2013 | Azamian et al. |
| 2013/0345670 A1 | 12/2013 | Rajagopalan et al. |
| 2014/0031773 A1 | 1/2014 | Mikkaichi |
| 2014/0074077 A1 | 3/2014 | Lane |
| 2014/0088529 A1 | 3/2014 | Bengtson |
| 2014/0121646 A1 | 5/2014 | Lodin et al. |
| 2014/0135661 A1 | 5/2014 | Garrison et al. |
| 2014/0163664 A1 | 6/2014 | Goldsmith |
| 2014/0187619 A1 | 7/2014 | Pasricha et al. |
| 2014/0255458 A1 | 9/2014 | Li et al. |
| 2014/0324037 A1 | 10/2014 | Hoey et al. |
| 2014/0371736 A1 | 12/2014 | Levin et al. |
| 2015/0045825 A1 | 2/2015 | Caplan |
| 2015/0141987 A1 | 5/2015 | Caplan et al. |
| 2015/0148738 A1 | 5/2015 | Caplan et al. |
| 2015/0359594 A1 | 12/2015 | Ben-Oren et al. |
| 2016/0081745 A1 | 3/2016 | Rajagopalan et al. |
| 2016/0310200 A1 | 10/2016 | Wang |
| 2017/0007324 A1 | 1/2017 | Kadamus et al. |
| 2017/0014596 A1 | 1/2017 | Rajagopalan et al. |
| 2017/0191035 A1 | 7/2017 | Sia et al. |
| 2017/0333122 A1 | 11/2017 | Rajagopalan et al. |
| 2018/0193078 A1 | 7/2018 | Rajagopalan et al. |

FOREIGN PATENT DOCUMENTS

| | | |
|---|---|---|
| CN | 101212932 A | 7/2008 |
| EP | 1698296 A1 | 9/2006 |
| EP | 1886634 A1 | 2/2008 |
| EP | 3071286 A1 | 9/2016 |
| JP | 2002503512 A | 2/2002 |
| JP | 2003520068 A | 7/2003 |
| JP | 2004500184 A | 1/2004 |
| JP | 2004180934 A | 7/2004 |
| JP | 2006509536 A | 3/2006 |
| JP | 2006136726 A | 6/2006 |
| JP | 2007502690 A | 2/2007 |
| JP | 2008515464 A | 5/2008 |
| JP | 2010142661 A | 7/2010 |
| JP | 2010533036 A | 10/2010 |
| JP | 2011517599 A | 6/2011 |
| JP | 2013543423 A | 12/2013 |
| JP | 2014503256 A | 2/2014 |
| KR | 20080013945 A | 2/2008 |
| WO | WO-9418896 A1 | 9/1994 |
| WO | WO-9912489 A2 | 3/1999 |
| WO | WO 02/07628 A2 | 1/2002 |
| WO | WO-02058577 A1 | 8/2002 |
| WO | WO 02/102453 A2 | 12/2002 |
| WO | WO-02096327 A2 | 12/2002 |
| WO | WO 2003/033045 A2 | 4/2003 |
| WO | WO-03092609 A2 | 11/2003 |
| WO | WO-2004064600 A2 | 8/2004 |
| WO | WO-2006020370 A2 | 2/2006 |
| WO | WO-2007044244 A2 | 4/2007 |
| WO | WO-2007067919 A2 | 6/2007 |
| WO | WO-2008002654 A2 | 1/2008 |
| WO | WO 2010/042461 A1 | 4/2010 |
| WO | WO-2010125570 A1 | 11/2010 |
| WO | WO 2011/060301 A1 | 5/2011 |
| WO | WO-2012009486 A2 | 1/2012 |
| WO | WO 2012/099974 A2 | 7/2012 |
| WO | WO 2013/130655 A1 | 9/2013 |
| WO | WO-2013134541 A2 | 9/2013 |
| WO | WO 2013/159066 A1 | 10/2013 |
| WO | WO 2014/022436 A1 | 2/2014 |
| WO | WO 2014/026055 A1 | 2/2014 |
| WO | WO-2014055997 A1 | 4/2014 |
| WO | WO-2014070136 A1 | 5/2014 |
| WO | WO-2015038973 A1 | 3/2015 |
| WO | WO-2015077571 A1 | 5/2015 |
| WO | WO-2015148541 A1 | 10/2015 |
| WO | WO-2016011269 A1 | 1/2016 |
| WO | WO-2017004432 A1 | 1/2017 |
| WO | WO-2018089773 A1 | 5/2018 |
| WO | WO-2019018362 A1 | 1/2019 |
| WO | WO-2019136240 A1 | 7/2019 |

OTHER PUBLICATIONS

International search report and written opinion dated Oct. 23, 2015 for PCT/US2015/040775.
European search report and search opinion dated Aug. 4, 2015 for EP Application No. 13755156.0.
International search report and written opinion dated Jun. 26, 2015 for PCT Application No. US2015/022293.
Office action dated Aug. 5, 2015 for U.S. Appl. No. 13/945,138.
U.S. Appl. No. 61/603,475, filed Feb. 27, 2012, Rajagopalan et al.
U.S. Appl. No. 61/635,810, filed Apr. 19, 2012, Caplan et al.
International search report and written opinion dated Feb. 20, 2015 for PCT Application No. US2014/711601.
International search report and written opinion dated Jun. 21, 2013 for PCT Application No. US2013/028082.
International search report and written opinion dated Jul. 13, 2012 for PCT Application No. US2012/021739.
International search report and written opinion dated Aug. 8, 2013 for PCT Application No. US2013/037485.
International search report and written opinion dated Nov. 8, 2013 for PCT Application No. US2013/052786.
International search report and written opinion dated Nov. 11, 2013 for PCT Application No. US2013/054219.

(56) References Cited

OTHER PUBLICATIONS

International search report and written opinion dated 12/24/2014 for PCT Application No. US2014/055514.
International search report and written opinion dated Dec. 30, 2013 for PCT Application No. US2013/063753.
International search report dated Dec. 3, 2014 for PCT Application No. US2014/040957.
Miyawaki, et al. Inhibition of gastric inhibitory polypeptide signaling prevents obesity. Nat Med. Jul. 2002;8(7):738-42. Epub Jun. 17, 2002.
Office action dated Mar. 12, 2015 for U.S. Appl. No. 13/945,138.
Rubino, et al. Potential of surgery for curing type 2 diabetes mellitus. Ann Surg. Nov. 2002;236(5):554-9.
Co-pending U.S. Appl. No. 14/956,710, filed Dec. 2, 2015.
European search report and search opinion dated Nov. 25, 2015 for EP Application No. 13777572.2.
Office action dated Nov. 30, 2015 for U.S. Appl. No. 13/945,138.
Office action dated Dec. 17, 2015 for U.S. Appl. No. 14/515,324.
U.S. Appl. No. 61/681,502, filed Aug. 9, 2012.
Chathadi, et al. The role of endoscopy in ampullary and duodenal adenomas. Gastrointest Endosc. Nov. 2015;82(5):773-81. doi: 10.1016/j.gie.2015.06.027. Epub Aug. 7, 2015.
Co-pending U.S. Appl. No. 15/156,585, filed May 17, 2016.
Co-pending U.S. Appl. No. 14/917,243, filed Mar. 7, 2016.
European search report and search opinion dated Mar. 8, 2016 for EP Application No. 13825257.2.
European search report and search opinion dated Mar. 17, 2016 for EP Application No. 13827149.9.
Office action dated Feb. 29, 2016 for U.S. Appl. No. 14/609,334.
Adams, et al. Theoretical design and evaluation of endoluminal ultrasound applicators for thermal therapy of pancreatic cancer under image guidance. AIP Conference Proceedings 1821, 110002 (2017); doi: http://dx.doi.org/10.1063/1.4977640.
Cherrington, et al. Hydrothermal Duodenal Mucosal Resurfacing: Role in the Treatment of Metabolic Disease. Gastrointest Endosc Clin N Am. Apr. 2017;27(2):299-311. doi: 10.1016/j.giec.2016.12.002.
Co-pending U.S. Appl. No. 15/683,713, filed Aug. 22, 2017.
Co-pending U.S. Appl. No. 15/812,969, filed Nov. 14, 2017.
European Search Report and Search Opinion dated Aug. 7, 2017 for European Patent Application No. EP14864511.2.
European Search Report and Search Opinion dated Aug. 7, 2017 for European Patent Application No. EP15768945.6.
European search report with written opinion dated Feb. 1, 2018 for EP Application No. 15822378.
European search report with written opinion dated Dec. 2, 2016 for EP Application No. 14807116.
Galvao Neto, et al. Endoscopic Duodenal Mucosal Resurfacing Improves Glycemic and Hepatic Parameters in Patients With Type 2 Diabetes: Data From a First-in-Human Study. Gastroenterology. 829. Apr. 2016, vol. 150, Issue 4, Supplement 1, p. S174. 1 page. DOI: http://dx.doi.org/10.1016/S0016-5085(16)30672-2.
International Search Report and Written Opinion dated Sep. 22, 2016 for International PCT Patent Application No. PCT/US2016/040512.
International search report with written opinion dated Jan. 9, 2018 for PCT/US2017/061074.
Notice of Allowance dated Jul. 7, 2017 for U.S. Appl. No. 15/274,764.
Notice of Allowance dated Sep. 14, 2017 for U.S. Appl. No. 15/274,809.
Office action dated Jan. 8, 2018 for U.S. Appl. No. 14/609,334.
Office Action dated Jan. 13, 2017 for U.S. Appl. No. 14/609,332.
Office Action dated Mar. 7, 2017 for U.S. Appl. No. 15/274,764.
Office Action dated Mar. 7, 2017 for U.S. Appl. No. 15/274,809.
Office action dated Mar. 19, 2018 for U.S. Appl. No. 14/470,503.
Office Action dated Mar. 23, 2017 for U.S. Appl. No. 13/945,138.
Office action dated Apr. 4, 2018 for U.S. Appl. No. 15/156,585.
Office action dated May 18, 2018 for U.S. Appl. No. 14/956,710.
Office Action dated May 31, 2017 for U.S. Appl. No. 15/274,764.
Office Action dated Jun. 21, 2017 for U.S. Appl. No. 14/515,324.
Office Action dated Jun. 21, 2017 for U.S. Appl. No. 14/609,334.
Office Action dated Jun. 30, 2017 for U.S. Appl. No. 14/470,503.
Office Action dated Sep. 23, 2016 for U.S. Appl. No. 14/515,324.
Office Action dated Oct. 7, 2016 for U.S. Appl. No. 13/945,138.
Office Action dated Nov. 2, 2017 for U.S. Appl. No. 15/156,585.
Office Action dated Nov. 15, 2016 for U.S. Appl. No. 14/609,334.
Office action dated Nov. 16, 2017 for U.S. Appl. No. 14/609,332.
Office action dated Dec. 18, 2017 for U.S. Appl. No. 14/515,324.
Office action dated Dec. 19, 2017 for U.S. Appl. No. 13/945,138.
Rajagopalan, et al. Endoscopic Duodenal Mucosal Resurfacing for the Treatment of Type 2 Diabetes: 6-Month Interim Analysis From the First-in-Human Proof-of-Concept Study. Diabetes Care Dec. 2016; 39(12): 2254-2261. https://doi.org/10.2337/dc16-0383.
Sarriá, et al. Morphometric study of the layers of the canine small intestine at five sampling sites. Vet J. Jun. 2012;192(3):498-502. doi: 10.1016/j.tvjl.2011.06.041. Epub Nov. 3, 2011.
Tomizawa, et al. Clinical Outcome of Endoscopic Mucosal Resection (EMR) of Sporadic, Non-Ampullary Duodenal Adenoma (SNADA) : Predictor Analysis of Safety and Efficacy From a High Volume U.S. Tertiary Referral Center. Gastrointestinal Endoscopy. 377. May 2017, vol. 85, Issue 5, Supplement, p. AB72. DOI: http://dx.doi.org/10.1016/j.gie.2017.03.089.
Van Baar, et al. Single Catheter for Duodenal Mucosal Resurfacing Demonstrates Similar Safety Profile with Improved Procedure Time when Compared to Original Dual Catheter: Multicenter Study of Subjects with Type 2 Diabetes. Gastroenterology. Apr. 2017vol. 152, Issue 5, Supplement 1, p. S825. DOI: http://dx.doi.org/10.1016/S0016-5085(17)32851-2.
"Office Action dated Jul. 11, 2018 for U.S. Appl. No. 14/917,243."
"Office action dated Sep. 7, 2018 for U.S. Appl. No. 14/609,332."
"Office action dated Oct. 4, 2018 for U.S. Appl. No. 14/515,324."
"Office action dated Nov. 2, 2018 for U.S. Appl. No. 14/609,334".
"Office action dated Dec. 18, 2018 for U.S. Appl. No. 14/470,503."
U.S. Appl. No. 15/406,572 Office Action dated Nov. 15, 2019.
U.S. Appl. No. 15/683,713 Notice of Allowance dated Nov. 27, 2019.
U.S. Appl. No. 14/470,503 Notice of Allowance dated Feb. 27, 2019.
U.S. Appl. No. 14/956,710 Notice of Allowance dated Jan. 9, 2019.
Co-pending U.S. Appl. No. 16/267,771, filed Feb. 5, 2019.
Co-pending U.S. Appl. No. 16/379,554, filed Apr. 9, 2019.
Co-pending U.S. Appl. No. 16/400,491, filed May 1, 2019.
Co-pending U.S. Appl. No. 16/438,362, filed Jun. 11, 2019.
EP12736438.8 The Extended European Search Report dated Nov. 22, 2016.
EP14844285.8 The Extended European Search Report dated Apr. 25, 2017.
Grikscheit, et al. Tissue-engineered small intestine improves recovery after massive small bowel resection. Ann Surg., 2004, 240:748-754.
PCT/US14/66829 International Search Report dated Feb. 20, 2015.
PCT/US2019/012338 International Search Report dated Apr. 15, 2019.
Semkova, et al. Autologous transplantation of genetically modified iris pigment epithelial cells: A promising concept for the treatment of age-related macular degeneration and other disorders of the eye. Proc Natl Acad Sci U S A. Oct. 1, 2002; 99(20): 13090-13095.
Sen, et al. Autologous transplantation of endothelial progenitor cells genetically modified by adeno-associated viral vector delivering insulin-like growth factor-1 gene after myocardial infarction. Hum Gene Ther. Oct. 2010;21(10):1327-34.
U.S. Appl. No. 15/683,713 Office Action dated Oct. 10, 2019.
"Office action dated Mar. 7, 19 for U.S. Appl. No. 13/945,138."
Final Office action dated Mar. 22, 2019 for U.S. Appl. No. 14/917,243.
Final Office action dated Apr. 5, 2019 for U.S. Appl. No. 14/609,334.
Final Office action dated Jun. 17, 2019 for U.S. Appl. No. 14/609,332.
Final Office action dated Jul. 10, 2019 for U.S. Appl. No. 15/274,948.
Office action dated May 16, 2019 for U.S. Appl. No. 14/515,324.
Office action dated Jun. 6, 2019 for U.S. Appl. No. 15/683,713.
U.S. Appl. No. 15/274,948 Office Action dated Nov. 20, 2018.
U.S. Appl. No. 15/406,572 Office Action dated Feb. 7, 2019.
Co-pending U.S. Appl. No. 16/798,117, filed Feb. 21, 2020.
U.S. Appl. No. 15/406,572 Office Action dated Apr. 14, 2020.

(56) References Cited

OTHER PUBLICATIONS

U.S. Appl. No. 14/515,324 Office Action dated Mar. 31, 2020.
U.S. Appl. No. 15/683,713 Notice of Allowance dated Mar. 10, 2020.
Co-pending U.S. Appl. No. 16/711,236, filed Dec. 11, 2019.
Co-pending U.S. Appl. No. 16/742,645, filed Jan. 14, 2020.
U.S. Appl. No. 13/945,138 Office Action dated Dec. 10, 2019.
U.S. Appl. No. 14/609,334 Office Action dated Jan. 8, 2020.
U.S. Appl. No. 15/917,480 Office Action dated Jan. 10, 2020.
U.S. Appl. No. 16/267,771 Office Action dated Feb. 6, 2020.
EP20150391.9 The Extended European Search Report dated Aug. 20, 2020.
U.S. Appl. No. 16/267,771 Notice of Allowance dated Aug. 10, 2020.
Co-pending U.S. Appl. No. 17/021,798, filed Sep. 15, 2020 by Rajagopalan; Harith et al.
EP20159816.6 The Extended European Search Report dated Aug. 17, 2020.
Co-pending U.S. Appl. No. 16/900,563, filed Jun. 12, 2020 by Kadamus, et al.
Co-pending U.S. Appl. No. 16/905,274, filed Jun. 18, 2020 by Rajagopalan, et al.
U.S. Appl. No. 14/917,243 Office Action dated Jun. 5, 2020.
U.S. Appl. No. 15/274,948 Notice of Allowance dated May 14, 2020.
Co-pending U.S. Appl. No. 17/095,108, inventors Rajagopalan; Harith et al., filed Nov. 11, 2020.
Co-pending U.S. Appl. No. 17/096,855, inventors Rajagopalan; Harith et al., filed Nov. 12, 2020.
Co-pending U.S. Appl. No. 17/110,720, inventors J.; Kadamus Christopher J. et al., filed Dec. 3, 2020.
PCT/US2018/042438 International Search Report dated Sep. 14, 2018.
U.S. Appl. No. 13/945,138 Notice of Allowance dated Dec. 22, 2020.
U.S. Appl. No. 14/515,324 Office Action dated Dec. 4, 2020.
U.S. Appl. No. 14/609,334 Notice of Allowance dated Dec. 10, 2020.
U.S. Appl. No. 14/609,334 Office Action dated Oct. 29, 2020.
U.S. Appl. No. 15/406,572 Notice of Allowance dated Oct. 28, 2020.
U.S. Appl. No. 15/917,480 Notice of Allowance dated Dec. 17, 2020.
U.S. Appl. No. 15/917,480 Office Action dated Nov. 20, 2020.
U.S. Appl. No. 16/711,236 Office Action dated Dec. 10, 2020.
U.S. Appl. No. 16/900,563 Notice of Allowance dated Dec. 17, 2020.
U.S. Appl. No. 16/900,563 Office Action dated Nov. 9, 2020.

* cited by examiner

METHODS, SYSTEMS AND DEVICES FOR PERFORMING MULTIPLE TREATMENTS ON A PATIENT

CROSS-REFERENCE TO RELATED APPLICATIONS

This application is a continuation of International Patent Application No. PCT/US2013/063753, filed Oct. 7, 2013, which claims the benefit of U.S. Provisional Application Ser. No. 61/710,318, filed Oct. 5, 2012, the entire content of which is incorporated herein by reference in its entirety.

This application is related to: International Patent Application Serial Number PCT/US2012/021739, entitled "Devices and Methods for the Treatment of Tissue", filed Jan. 18, 2012; International Patent Application Serial Number PCT/US2013/028082, entitled "Heat Ablation Systems, Devices and Methods for the Treatment of Tissue", filed Feb. 27, 2013; International Patent Application Serial Number PCT/US2013/037485, entitled "Tissue Expansion Devices, Systems and Methods", filed Apr. 19, 2013; International Patent Application Serial Number PCT/US2013/052786, entitled "Electrical Energy Ablation Systems, Devices and Methods for the Treatment of Tissue", filed Jul. 30, 2013; and International Patent Application Serial Number PCT/US2013/054219, entitled "Ablation Systems, Device and Methods for the Treatment of Tissue", filed Aug. 8, 2013; the contents of which are each incorporated herein by reference in their entirety.

TECHNICAL FIELD

The embodiments disclosed herein relate generally to systems, devices and methods for treating tissue, particularly gastrointestinal tissue.

BACKGROUND OF THE INVENTION

Diabetes is a metabolic disease in which a person develops high blood sugar because the person's body does not produce enough insulin or the cells of the body are incapable of effectively responding to the produced insulin. Primarily, diabetes is of two types: Type 1 and Type 2. Type 1 diabetes results from the body's autoimmune destruction of pancreatic beta cells and, consequently, the body's failure to produce enough insulin. Type 2 diabetes is a complex metabolic derangement related to obesity that causes hyperglycemia through insulin resistance (in which the body's cells fail to properly utilize the produced insulin) and eventually inadequate insulin production to meet the body's needs.

Currently, there are several procedures aimed at treating diabetes based on the above concept. The procedures require major surgery, removal of portions of the GI tract, and/or long-term implants. As with any major surgery, gastric bypass surgery carries a risk of complications.

Devices have been developed to delivery energy to the body. For example, cardiac ablation devices have been designed to delivery ablative energy to coronary tissue. Additionally, urethral resection devices have been designed to burn or cut away portions of a prostate. Each of these technologies has been modified and adapted toward effective usage in the particular portion of the body to be treated as well as the particular disease to be treated.

There is a need for systems and methods that can provide a therapeutic treatment of the GI tract by the application of energy to the GI tract. Specifically, there is a need to provide a treatment of diabetes with a procedure in the GI tract that is less invasive than gastric bypass surgery and has other advantages for patients.

BRIEF SUMMARY OF THE INVENTION

According to one aspect of the present inventive concepts, a method for treating a patient comprises performing a first treatment comprising treating a first portion of tissue comprising at least duodenal tissue and performing a second treatment comprising treating a second portion of tissue comprising at least gastrointestinal tissue, where the second tissue portion is treated at least twenty-four hours after the first tissue portion is treated.

The method can be performed to treat a disease or disorder selected from the group consisting of: diabetes; obesity or otherwise being overweight; hypercholesterolemia; exercise intolerance; psoriasis; and combinations of these.

The first treatment can comprise an ablation treatment, and the second treatment can comprise a non-ablative treatment. The ablation treatment can comprise a treatment selected from the group consisting of: delivery of thermal energy from a balloon filled with fluid at an ablative temperature; RF energy ablation; delivery of an ablative fluid directly to tissue; cryoablation; delivery of laser energy; delivery of sound energy such as subsonic sound energy or ultrasonic sound energy; and combinations of these.

The first treatment can comprise a non-ablative treatment. The first treatment can comprise a treatment selected from the group consisting of: mechanical removal of mucosal tissue; sclerosant injection into the submucosa; radioactive seed deposition; chemical spray such as an acid spray; pharmacologic administration such as drug delivery via an agent-eluting balloon; and combinations of these.

The first treatment can further comprise expanding one or more layers of duodenal tissue. The one or more layers of duodenal tissue can include duodenal submucosal tissue.

The first treatment can comprise multiple treatment steps. The multiple treatment steps can include: multiple sequential deliveries of energy to tissue; multiple sequential deliveries of ablative fluid to tissue; multiple sequential abrasions of tissue; and combinations of these. The method can further comprise expanding one or more layers of tissue. The method can further comprise performing two or more expansions of one or more layers of tissue.

The first treatment can further comprise implanting a device in at least a portion of the duodenum. The second treatment can further comprise removing at least a portion of the implanted device.

The first treatment can comprise a treatment which is stopped due to a procedural complication. The procedural complication can be selected from the group consisting of: bleeding; patient discomfort; pancreatic injury; intestinal perforation; unintended duodenal mechanical damage, such as unintended abrasion; excess thermal dose delivery; excess mucosal interface temperature; and combinations of these. The first treatment can comprise a treatment which is stopped due to a procedural time limit threshold being exceeded.

The second treatment can comprise an ablative treatment. The ablation treatment can comprise a treatment selected from the group consisting of: delivery of thermal energy from a balloon filled with fluid at an ablative temperature; RF energy ablation; delivery of an ablative fluid directly to tissue; cryoablation; delivery of laser energy; delivery of sound energy such as subsonic sound energy or ultrasonic sound energy; and combinations of these.

The second treatment can comprise a non-ablative treatment. The second treatment can comprise a treatment selected from the group consisting of: mechanical removal of mucosal tissue; sclerosant injection into the submucosa; radioactive seed deposition; chemical spray such as an acid spray; pharmacologic administration such as drug delivery via an agent-eluting balloon; and combinations of these.

The patient can receive an improved therapeutic benefit after the second treatment is performed. The method can comprise a third treatment comprising treating a third portion of tissue comprising at least gastrointestinal tissue, wherein the patient receives an improved therapeutic benefit after the third treatment is performed.

The second treatment can be performed at least 1 week after the first treatment is performed, at least 1 month after the first treatment is performed, at least 6 weeks after the first treatment is performed, at least 3 months after the first treatment is performed, at least 6 months after the first treatment is performed, or at least 1 year after the first treatment is performed.

The second treatment can be performed after a time period has elapsed since the first procedure, and the time period duration can be determined prior to the performance of the first procedure.

The first treatment can comprise delivery of a first energy delivery profile, and the second treatment can comprise delivery of a second energy delivery profile, where the first energy delivery profile and the second energy delivery profile are similar. The first energy delivery profile and the second energy delivery profile can comprise similar energy types and/or similar delivered energy amounts.

The first treatment can comprise delivery of a first energy delivery profile, and the second treatment can comprise delivery of a second energy delivery profile, where the first energy delivery profile and the second energy delivery profile are dissimilar. The first energy delivery profile and the second energy delivery profile can comprise dissimilar energy types and/or dissimilar delivered energy amounts.

The second treatment can further comprise expanding one or more layers of duodenal tissue. The one or more layers of duodenal tissue can include duodenal submucosal tissue. Additionally, the first treatment can further comprise expanding one or more layers of duodenal tissue. The first treatment tissue expansion can differ from the second treatment tissue expansion, for example, the difference can comprise different values of a parameter selected from the group consisting of: total volume of fluid injected; amount of tissue area expanded; location of tissue expanded; expansion fluid type; expansion device configuration; and combinations of these.

The method can comprise a third treatment comprising treating a third tissue portion comprising at least gastrointestinal tissue, where the third tissue treatment can be performed at least one day after the second treatment is performed. The duration of time between the first treatment and the second treatment can be similar to the duration of time between the second treatment and the third treatment.

The method can further comprise performing multiple additional treatments each comprising treating tissue portions comprising at least gastrointestinal tissue, where the multiple tissue treatments can be performed at least one day after the second treatment is performed. The multiple additional treatments can be performed at relatively regular time intervals, for example time intervals of 6 months to 5 years.

The first tissue portion can comprise at least a portion of the mucosal layer of the duodenum. The first tissue portion can further comprise at least a portion of tissue selected from the group consisting of: jejunal mucosa; ileal mucosa; gastric mucosa; and combinations of these. The first tissue portion can comprise approximately 67% or less of the duodenal mucosa, for example approximately 50% or less of the duodenal mucosa. The second tissue portion can comprise substantially the remainder of the duodenal mucosa. The second treatment can further comprise treating at least a portion of the first tissue portion. The first tissue portion can comprise less than 100% of the duodenal mucosa. The second tissue portion comprises a larger volume of tissue than the first tissue portion. The first tissue portion can comprise less than 50% of the duodenal mucosa, and the second tissue portion can comprise more than 50% of the duodenal mucosa. The first tissue portion can comprise at least a full circumferential portion of duodenal mucosa. The first tissue portion can comprise a 45° to 350° circumferential portion of duodenal tissue, for example a 300° to 350° circumferential portion of duodenal tissue.

The first treatment can be constructed and arranged to prevent formation of a full circumferential scar.

The first tissue portion can comprise a volume of tissue below a threshold, and the threshold can be selected to prevent the occurrence of an adverse event. The second tissue portion can comprise a larger volume of tissue than the first tissue portion. The second tissue portion can comprise a different volume of tissue than the first tissue portion. The threshold can be selected to prevent or reduce hypoglycemia; prevent or reduce damage to tissue beyond the mucosal layer of the gastrointestinal tract; prevent or reduce damage to tissue beyond the superficial submucosa; prevent or reduce damage to tissue beyond the deep submucosa; and combinations of these.

The first tissue portion comprises a volume of tissue below a threshold, and the threshold is selected to reduce tissue healing duration. The first tissue portion can comprise a longitudinal portion of duodenum comprising a length less than 6 inches, or a length less than 4 inches.

The second tissue portion can comprise a second tissue volume and the first tissue portion can comprise a first tissue volume similar to the second tissue volume. The second tissue portion can comprise a second anatomical location and the first tissue portion can comprise a first anatomical location similar to the second anatomical location. The first anatomical location and the second anatomical location can be similar to improve the therapeutic benefit to the patient and/or to treat tissue that was untreated after the first treatment.

The second tissue portion can be dissimilar to the first tissue portion. The second tissue portion can comprise a second tissue volume and the first tissue portion can comprise a first tissue volume dissimilar to the second tissue volume. The second tissue portion can comprise a different axial segment of duodenum than the first tissue portion and/or a different circumferential segment than the first tissue portion. The second tissue portion can comprise tissue segments that border the first tissue portion. The second tissue portion can comprise additional tissue portions not included in the first tissue portion, the additional tissue portions selected from the group consisting of: jejunal mucosa; ileal mucosa; gastric mucosa; and combinations of these, for example where the first tissue portion does not comprise non-duodenal tissue.

The method can further comprise performing a diagnostic procedure to produce diagnostic results. The diagnostic procedure can be performed prior to and/or after the first treatment.

The diagnostic procedure can comprise a clinical test, for example where the clinical test can comprise an assessment of a parameter selected from the group consisting of: body weight; body mass index (BMI); blood pressure; and combinations of these.

The diagnostic procedure can comprise an efficacy serum test, for example where the serum test comprises an assessment of a parameter selected from the group consisting of: hemoglobin A1c (HgbAa1c); post-meal or post-glucose tolerance test glucose; HOMA-IR; insulin; C-peptide; glucagon; GIP; GLP-1; LDL; HDL; triglycerides; and combinations of these.

The diagnostic procedure can comprise a fasting serum test, for example where the fasting serum test comprises an assessment of a parameter selected from the group consisting of: glucose; insulin; HOMA-IR; C-peptide; glucagon; GIP; GLP-1; LDL; HDL; triglycerides; and combinations of these.

The diagnostic procedure can comprise a safety serum test, for example where the safety serum test comprises an assessment of a parameter selected from the group consisting of: C-reactive protein; amylase; lipase; AST; ALT; total bilirubin; and combinations of these.

The diagnostic procedure can comprise a serum marker assessment, for example where the serum marker assessment is performed in a fed or fasting state. The diagnostic results can be used to determine a second tissue portion parameter selected from the group consisting of: second tissue portion anatomical location; second tissue portion volume; and combinations of these. The diagnostic results can be used to determine the duration of time between the first treatment and the second treatment. The results can comprise an assessment of serum marker levels over time. The serum marker assessment can comprise an assessment of adverse effects of the first treatment. The serum marker assessment can comprise a measurement of a compound selected from the group consisting of: amylase; lipase; glucose, insulin, C-peptide, C-reactive protein, creatine kinase, lactate; and combinations of these. The second treatment can comprise a delivery of energy that is reduced from a first treatment energy delivery based on the serum marker assessment indication of an adverse event.

The diagnostic procedure can comprise an intestinal biopsy and histological evaluation. The histological evaluation can comprise an assessment of a parameter selected from the group consisting of: depth of viability staining; enteroendocrine cell population; GIP-producing cell population; GLP-1 producing cell population; glucagon-producing cell quantity; surface topology of the duodenal mucosa; presence, absence, or substantial reduction in depth of plicae circulares; and combinations of these.

The diagnostic procedure can comprise a patient weight measurement. The second treatment can differ from the first treatment based on the weight measurement, for example where the difference in the second treatment comprises treating at least one of the gastric mucosa or the ileal mucosa.

The diagnostic procedure can comprise a cholesterol parameter measurement. The second treatment can differ from the first treatment based on the cholesterol measurement, for example where the difference in the second treatment comprises treating at least one of the gastric mucosa or the ileal mucosa.

The diagnostic procedure can comprise an assessment of the depth of tissue treated during the first treatment. The depth of tissue treated can comprise a depth of ablation provided during the first treatment. The diagnostic procedure can comprise a viability staining procedure. The second treatment can differ from the first procedure if the viability staining procedure produces results exceeding a threshold, for example where the second treatment comprises an energy delivery parameter that is increased from a first treatment energy delivery parameter.

The diagnostic procedure comprises an assessment of a pattern of mucosal regrowth, for example where the second tissue portion comprises tissue extending from the first tissue portion.

The diagnostic procedure can comprise the performance of at least one biopsy. The at least one biopsy can be performed at a time selected from the group consisting of: before the first treatment; between the first and second treatments; after the second treatment; and combinations of these. The at least one biopsy can comprise a first biopsy of a treated tissue volume and a second biopsy of a non-treated tissue volume. The second tissue portion can be selected based on results of the biopsy, for example where the second tissue portion comprises tissue proximal or distal to the first tissue portion based on the biopsy results.

The diagnostic procedure can comprise an assessment of a pattern of intestinal healing by endoscopic visualization. The second tissue portion can comprise tissue from the first treatment that retains prominent plicae circulares.

The second treatment comprises one or more treatment parameters whose value is determined based on the diagnostic procedure results. The one or more second treatment parameters can comprise the anatomical location of the second portion of tissue; a depth of treatment parameter; a volume of the second portion of tissue to be treated in the second treatment; and combinations of these. The diagnostic results can be used to determine the duration of time between the first treatment and the second treatment. The one or more second treatment parameters can comprise an energy delivery parameter, for example an energy delivery parameter selected from the group consisting of: temperature of ablative fluid to be delivered such as temperature of fluid to be delivered to a nozzle or to an expandable reservoir such as a balloon; type of ablative fluid to be delivered; rate of ablative fluid to be delivered; volume of ablative fluid to be delivered; type of energy to be delivered such as RF energy, thermal energy and/or mechanical energy; quantity of energy to be delivered such as a cumulative number of joules of energy to be delivered and/or peak amount of energy to be delivered; types and levels of combinations of energies to be delivered; energy delivery duration; pulse width modulation percentage of energy delivered; temperature of a cooling fluid to be delivered; temperature of a priming fluid to be delivered; flow rate of a fluid to be delivered; volume of a fluid to be delivered; number of reciprocating motions for an energy delivery element to transverse; temperature for a treatment assembly such as target temperature or maximum temperature; insufflation pressure; insufflation duration; and combinations of these.

The second tissue portion can be selected based on the diagnostic procedure results. The second tissue portion can comprise a volume greater than a volume of the first tissue portion, and the second tissue portion volume is sized based on the diagnostic results.

The diagnostic results can comprise data collected prior to the first treatment and data collected after the first treatment. The diagnostic results can comprise a magnitude of change of a measured parameter, and the second portion of tissue can comprise a larger volume than the first portion of tissue when the magnitude of change of the measured parameter is below a threshold. The diagnostic results can comprise a magnitude of change of a measured parameter, and the second portion of tissue can comprise a smaller volume than the first portion of tissue when the magnitude of change of the measured parameter is above a threshold.

The first tissue portion can comprise less than 50% of the duodenal mucosa. The diagnostic procedure can be performed after the first treatment, and the second treatment can differ from the first treatment based on the diagnostic results, for example where the second tissue portion comprises greater than 90% of the duodenal mucosa.

The diagnostic procedure can comprise an assessment of mucosal regrowth. The second treatment can differ from the first treatment based on the mucosal regrowth assessment. The mucosal regrowth assessment can produce an assessment of mucosal regrowth rate, and the second tissue portion can comprise a longer length of tissue than the first tissue portion when the mucosal regrowth rate is above a threshold, or the second tissue portion can comprise a shorter length of tissue than the first tissue portion when the mucosal regrowth rate is below a threshold. The regrowth assessment can comprise an assessment of the continuity of mucosal regrowth and/or an assessment of the quality of mucosal regrowth, for example an assessment of the presence of fully reconstituted villous structures. The regrowth assessment can be performed between 3 and 7 days from the performance of the first treatment.

The method can further comprise performing a submucosal expansion procedure, and the diagnostic procedure comprises an assessment of submucosal expansion achieved after the submucosal expansion procedure is performed, for example where the assessment comprises a measure of a parameter selected from the group consisting of: area of expansion; depth of expansion; safety of expansion; effectiveness of expansion; and combinations of these.

According to another aspect of the present inventive concepts a system for treating a patient comprises a first treatment device constructed and arranged to treat a first portion of tissue comprising duodenal tissue and a second treatment device constructed and arranged to treat a second portion of tissue comprising gastrointestinal tissue, where the second portion of tissue is treated at least twenty-four hours after the first portion of tissue is treated.

The first treatment device and the second treatment device can be similar or dissimilar. The first treatment device can deliver a first form of energy and the second treatment device can deliver a second form of energy, similar to or different from the first. The first treatment device can comprise a first treatment element and the second treatment device can comprise a second treatment element, similar to or different from the first. The first treatment element can treat an area of tissue with a first magnitude and the second treatment element can treat an area of tissue with a second magnitude, similar to or different from the first. The first treatment device can comprise at least one of a different length or different diameter than the second treatment device.

According to another aspect of the present inventive concepts, a method for treating a patient comprises performing a first treatment comprising treating a first portion of tissue comprising at least duodenal tissue, performing a diagnostic procedure to produce diagnostic results, and performing a second treatment comprising treating a second portion of tissue comprising at least gastrointestinal tissue, where the second treatment is based on the diagnostic results.

According to another aspect of the present inventive concepts, a system for treating a patient comprises a first device constructed and arranged to treat a first portion of tissue comprising at least duodenal tissue, a second device constructed and arranged to treat a second portion of tissue comprising at least gastrointestinal tissue, and a diagnostic tool constructed and arranged to produce diagnostic results, where the second device is constructed and arranged to treat the second portion of tissue based on the diagnostic results.

BRIEF DESCRIPTION OF THE DRAWINGS

The advantages of the technology described above, together with further advantages, may be better understood by referring to the following description taken in conjunction with the accompanying drawings. The drawings are not necessarily to scale, emphasis instead generally being placed upon illustrating the principles of the technology.

DETAILED DESCRIPTION OF THE DRAWINGS

Figure 1:
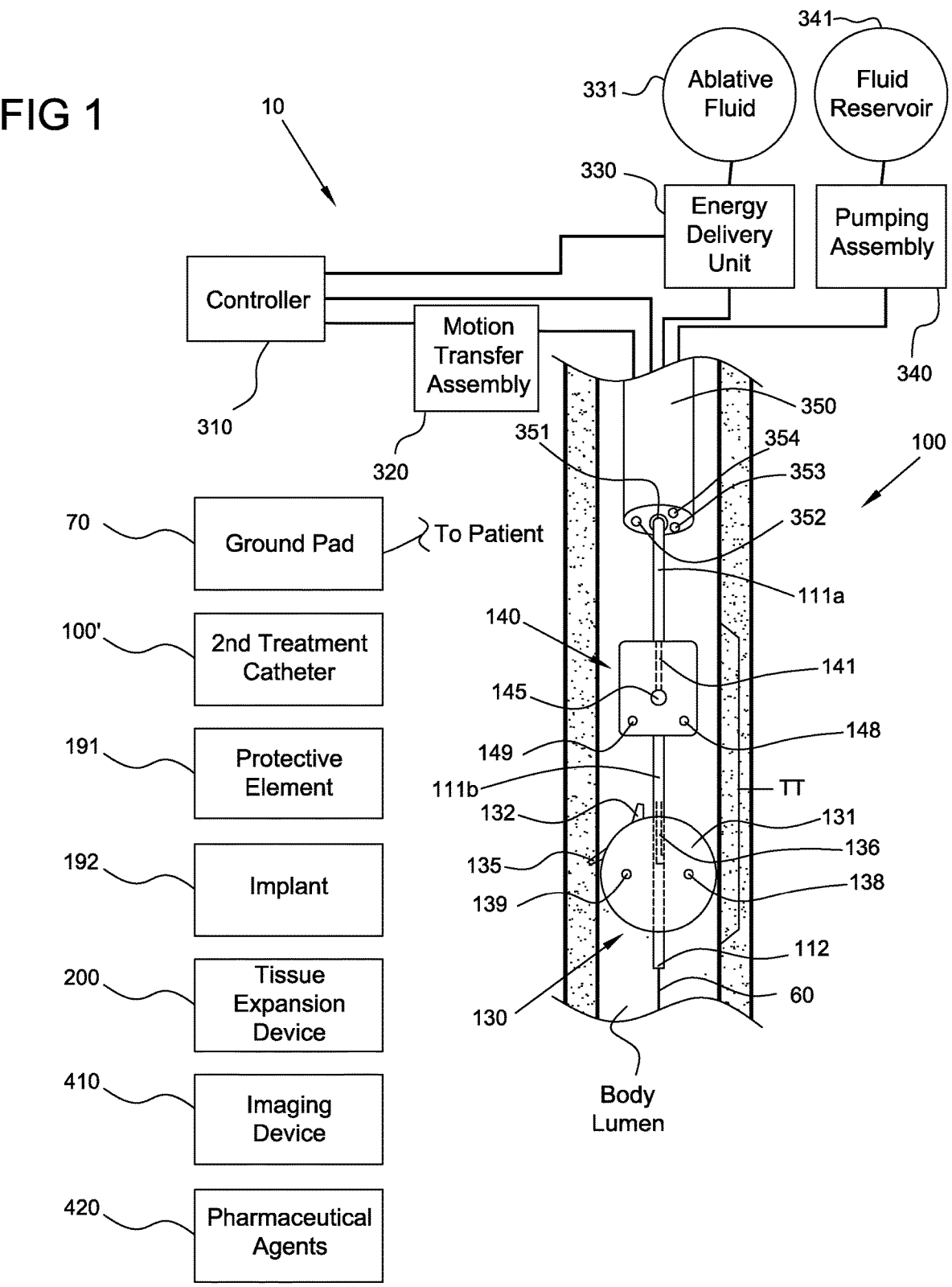
FIG. 1 is a schematic view of a system for ablating or otherwise treating target tissue, consistent with the present inventive concepts.

Reference will now be made in detail to the present embodiments of the inventive concepts, examples of which are illustrated in the accompanying drawings. Wherever practical, the same reference numbers will be used throughout the drawings to refer to the same or like parts.

The terminology used herein is for the purpose of describing particular embodiments and is not intended to be limiting of the inventive concepts. As used herein, the singular forms "a," "an" and "the" are intended to include the plural forms as well, unless the context clearly indicates otherwise.

It will be further understood that the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") when used herein, specify the presence of stated features, integers, steps, operations, elements, and/or components, but do not preclude the presence or addition of one or more other features, integers, steps, operations, elements, components, and/or groups thereof.

It will be understood that, although the terms first, second, third etc. may be used herein to describe various limitations, elements, components, regions, layers and/or sections, these limitations, elements, components, regions, layers and/or sections should not be limited by these terms. These terms are only used to distinguish one limitation, element, component, region, layer or section from another limitation, element, component, region, layer or section. Thus, a first limitation, element, component, region, layer or section discussed below could be termed a second limitation, element, component, region, layer or section without departing from the teachings of the present application.

It will be further understood that when an element is referred to as being "on" or "connected" or "coupled" to another element, it can be directly on or above, or connected or coupled to, the other element or intervening elements can be present. In contrast, when an element is referred to as being "directly on" or "directly connected" or "directly coupled" to another element, there are no intervening elements present. Other words used to describe the relationship between elements should be interpreted in a like fashion (e.g., "between" versus "directly between," "adjacent" versus "directly adjacent," etc.). When an element is referred to herein as being "over" another element, it can be over or under the other element, and either directly coupled to the other element, or intervening elements may be present, or the elements may be spaced apart by a void or gap.

The term "and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

As described herein, room pressure shall mean pressure of the environment surrounding the systems and devices of the present inventive concepts. Positive pressure includes pressure above room pressure or a pressure that is greater than another pressure, such as a positive differential pressure across a fluid pathway component such as a valve. Negative pressure includes pressure below room pressure or a pressure that is less than another pressure, such as a negative differential pressure across a fluid component pathway such as a valve. Negative pressure can include a vacuum but does not imply a pressure below a vacuum.

As used herein, the term "ablative fluid" refers to one or more fluids whose chemical properties (at room temperature, body temperature or otherwise) cause tissue necrosis or another desired tissue treatment. "Ablative fluid" shall also refer to any fluid at a sufficiently high or low temperature to cause a desired modification of tissue, such as tissue ablation. The hot or cold ablative fluid may be delivered directly to a tissue surface to treat tissue, or it may be delivered to a reservoir such as a balloon configured to treat tissue via contact (e.g. add to or remove sufficient heat from the balloon contacted tissue to cause tissue necrosis).

It is an object of the present inventive concepts to provide systems, methods and devices for safely and effectively ablating or otherwise treating a volume of tissue (the "target tissue"), such as to treat a patient disease or disorder. The target tissue can comprise one or more layers of a portion of tubular or non-tubular tissue, such as tissue of an organ or tissue of the gastrointestinal (GI) tract of a patient. The systems and devices of the present inventive concepts include one or more treatment devices configured to treat the target tissue, such as one or more devices including a treatment assembly. Each treatment assembly can comprise at least one treatment element such as a balloon configured to receive ablative fluid, one or more electrodes configured to deliver RF energy, and/or one or more fluid delivery elements configured to deliver an ablative fluid directly to tissue. Numerous forms of treatment assemblies and treatment elements can be included. In some embodiments, the treatment assemblies and/or the one or more treatment elements contained therein are configured as described in applicant's co-pending International PCT Application Serial Number PCT/US12/21739, entitled "Devices and Methods for the Treatment of Tissue", filed Jan. 18, 2012, the contents of which is incorporated herein by reference in its entirety.

In some embodiments, two or more clinical procedures are performed in which one or more volumes of target tissue are treated in each clinical procedure. For example, a second clinical procedure can be performed at least twenty-four hours after the first clinical procedure. The first and second clinical procedures can be performed using similar or dissimilar methods, and they can be performed using similar or dissimilar devices. The first and second clinical procedures can treat similar or dissimilar volumes of target tissue. In some embodiments, the first and second clinical procedures can include the treatment of contiguous and/or overlapping regions of the GI tract either in the circumferential and/or axial dimensions. In other embodiments, the first and second clinical procedures can include the treatment of disparate regions of the GI tract (such as disparate regions of the duodenum, ileum, and/or stomach). The first and second clinical procedures can be performed using similar or dissimilar treatment devices. The first and second clinical procedures can comprise similar or dissimilar deliveries of energy to treat the target tissue. The second clinical procedure can be performed based on diagnostic results collected after the first clinical procedure has been performed.

Each treatment assembly of the present inventive concepts can be configured to treat target tissue in one or more locations of the patient, such as one or more contiguous or discontiguous tissue locations. The target tissue comprises a three dimensional volume of tissue, and can include a first portion, a treatment portion, whose treatment has a therapeutic benefit to a patient; as well as a second portion, a "safety-margin" portion, whose treatment has minimal or no adverse effects to the patient. Non-target tissue can be identified (e.g. prior to and/or during the medical procedure), wherein the non-target tissue comprises tissue whose treatment by the treatment assembly should be reduced or avoided such as to reduce or prevent an undesired effect.

The target tissue treatment can cause one or more effects to the target tissue such as an effect selected from the group consisting of: modification of cellular function; cell death; apoptosis; instant cell death; cell necrosis; denaturing of cells; removal of cells; and combinations of these. In some embodiments, the target tissue treatment is configured to create scar tissue. Target tissue can be selected such that after treatment the treated target tissue and/or the tissue that replaces the target tissue functions differently than the pre-treated target tissue, such as to have a therapeutic benefit. The modified and/or replacement tissue can have different secretions and/or quantities of secretions than the pre-treated target tissue, such as to treat diabetes and/or obesity. The modified and/or replacement tissue can have different absorptive properties than the target tissue, such as to treat diabetes, obesity and/or hypercholesterolemia. The modified and/or replacement tissue can have a different surface topography than the target tissue, such as a modification of the topography of the inner wall of the GI tract that includes a smoothing or flattening of its inner surface. The effect of the treatment can occur acutely, such as within twenty-four hours, or after longer periods of time such as greater than twenty-four hours or greater than one week.

Target tissue to be treated can comprise two or more tissue portions, such as a first tissue portion treated with a first treatment and/or a first treatment assembly, and a second tissue portion treated with a second treatment and/or a second treatment assembly. The first and second treatments can be performed in the same clinical procedure, or in different clinical procedures (e.g. procedures performed on different days). The first and second tissue portions can be directly adjacent and they can contain overlapping portions of tissue. The first and second treatment and/or treatment assemblies can be similar or dissimilar. Dissimilarities can include type and/or amount of energy to be delivered by an energy delivery based treatment assembly. Other dissimilarities can include but are not limited to: target tissue area treated; target tissue volume treated; target tissue length treated; target tissue depth treated; target tissue circumferential portion treated; ablative fluid type, volume and/or temperature delivered to a reservoir such as a balloon; ablative fluid type, volume and/or temperature delivered directly to tissue; energy delivery type; energy delivery rate and/or amount; peak energy delivered; average temperature of target tissue achieved during target tissue treatment; maximum temperature achieved during target tissue treatment; temperature profile of target tissue treatment; duration of target tissue treatment; and combinations of these.

Target tissue can include tissue of the duodenum, such as tissue including all or a portion of the mucosal layer of the duodenum (e.g. including all or a portion of the plicae circulares of the mucosal layer), such as to treat diabetes and/or obesity while leaving the duodenum anatomically connected after treatment. Replacement tissue can comprise cells that have migrated from one or more of: gastric mucosa; jejunal mucosa; an untreated portion of the duodenum whose mucosal tissue functions differently than the treated mucosal tissue functions prior to treatment; and combinations of these. Replacement tissue can include one or more tissue types selected from the group consisting of: scar tissue; normal intestinal mucosa; gastric mucosa; and combinations of these. In some embodiments, target tissue includes a treatment portion comprising the mucosal layer of the duodenum, and a safety-margin portion comprising a near-full or partial layer of the submucosal layer of the duodenum. In some embodiments, the target tissue comprises nearly the entire length of the mucosal layer of the duodenum, and can include a portion of the pylorus contiguous with the duodenal mucosa and/or a portion of the jejunum contiguous with the duodenal mucosa. Treatment of duodenal tissue can be performed to treat a disease and/or disorder selected from the group consisting of: diabetes; obesity; insulin resistance; a metabolic disorder and/or disease; and combinations of these. A near full circumferential portion (e.g. approximately 360°) of the mucosal layer of one or more segments of gastrointestinal tissue can be treated. In some embodiments, less than 360° of tubular tissue is treated, such as one or more circumferential portions less than 350°, or between 300° and 350°, such as to prevent a full circumferential scar from being created.

Target tissue can be selected to treat two or more patient diseases or disorders, such as two or more patient diseases or disorders that are described herein.

Target tissue can comprise tissue of the terminal ileum, such as to treat hypercholesterolemia and/or diabetes. In these embodiments, the target tissue can extend into the proximal ileum and/or the colon.

Target tissue can comprise gastric mucosal tissue, such as tissue regions that produce ghrelin and/or other appetite regulating hormones, such as to treat obesity and/or an appetite disorder.

Target tissue can comprise bladder wall tissue, such as to treat a disease and/or disorder selected from the group consisting of: interstitial cystitis; bladder cancer; bladder polyps; pre-cancerous lesions of the bladder; and combinations of these.

Target tissue can comprise tissue selected from the group consisting of: large and/or flat colonic polyps; margin tissue remaining after a polypectomy; and combinations of these. These tissue locations can be treated to treat residual cancer cells.

Target tissue can comprise airway lining tissue, such as to treat a disease and/or disorder selected from the group consisting of: bronchoalveolar carcinoma; other lung cancers; pre-cancerous lung lesions; and combinations of these.

Target tissue can comprise at least a portion of the intestinal tract afflicted with inflammatory bowel disease, such that Crohn's disease and/or ulcerative colitis can be treated.

Target tissue can comprise tissue of the oral cavity, such as to treat one or more of: oral cancers and a pre-cancerous lesion of the oral cavity.

Target tissue can comprise tissue of the nasopharynx, such as to treat nasal polyps.

Target tissue can comprise gastrointestinal tissue selected to treat Celiac disease and/or to improve intestinal barrier function.

The treatment assemblies, systems, devices and methods of the present inventive concepts can be configured to avoid ablating or otherwise adversely affecting certain tissue, termed "non-target tissue" herein. Depending on the location of tissue intended for treatment (i.e. target tissue), different non-target tissue can be applicable. In certain embodiments, non-target tissue can comprise tissue selected from the group consisting of: gastrointestinal adventitia; duodenal adventitia; the tunica serosa; the tunica muscularis; the outermost partial layer of the submucosa; ampulla of Vater such as during mucosal treatment proximate the ampulla of Vater; pancreas; bile duct; pylorus; and combinations of these.

The treatment assemblies and expandable elements of the present inventive concepts can be configured to automatically and/or manually expand in at least a radial direction. Typical expandable elements include but are not limited to: an inflatable balloon; a radially expandable cage or stent; one or more radially deployable arms; an expandable helix; an unfurlable compacted coiled structure; an unfurlable sheet; an unfoldable compacted structure; and combinations of these. In some embodiments, the expandable elements can comprise a radially expandable tube, such as a sheet of material resiliently biased in a radially expanded condition that can be compacted through a furling operation, or a sheet of material resiliently biased in a radially compact condition that can be expanded through an unfurling operation. The expandable elements can comprise a foldable sheet, such as a sheet configured to be folded to be radially compacted and/or to be unfolded to radially expand. In some embodiments, the expandable elements expand to contact tissue, such as to expand to a diameter similar to the diameter of the luminal wall tissue into which the expandable element has been placed. In some embodiments, the expandable elements expand to be closer to wall tissue, but remain at a distance (e.g. a fixed or pre-determined distance) from the tissue surface. In some embodiments, the expandable elements expand to be larger than the diameter of the luminal wall tissue into which the expandable element has been placed, such as to improve the quality of the apposition of the expandable element against the uneven surface of the tissue. In these embodiments, the fully expanded diameter of the expandable elements would be configured to avoid a diameter large enough to cause lasting mechanical damage to the apposed tissue and/or to tissue proximate the apposed tissue.

Each device of the present inventive concepts can include one or more treatment elements configured to treat at least a portion of target tissue. Each device can include one or more fluid delivery elements, such as one or more nozzles configured to deliver fluid to tissue. The fluid delivery elements can be constructed and arranged to deliver fluid to perform a function selected from the group consisting of: expanding one or more tissue layers; warming or cooling tissue; removing debris or other substance from a tissue surface; treating target tissue; and combinations of these. Each of the expandable assemblies of the present inventive concepts can include one or more other functional elements, such as are described in reference to the figures herebelow. The treatment elements, fluid delivery elements, and/or other functional elements can be mounted on, within (e.g. within the wall) and/or inside of an expandable element such as a balloon or expandable cage. In some embodiments, one or more functional element(s) is not mounted to an expandable element, such as those attached to a shaft or other non-expandable treatment device component.

In some embodiments, the treatment device comprises at least one treatment element configured to ablate target tissue. Examples of ablation elements include but are not limited to: an expandable reservoir such as a balloon configured to receive fluid at a temperature sufficient to ablate tissue; fluid delivery elements configured to deliver ablative fluid directly to target tissue; a radiofrequency (RF) energy delivery element such as one or more electrodes; an ultrasonic transducer such as one or more piezo crystals configured to ablate tissue; a laser energy delivery element such as one or more optical fibers and/or laser diodes; a rotating ablation element; a circumferential array of ablation elements; and combinations of these.

The balloons of the present inventive concepts can be divided into two general categories: those that are composed of a substantially elastic material, such as silicone, latex, low-durometer polyurethane, and the like; and those that are composed of a substantially inelastic material, such as polyethylene terephthalate (PET), nylon, high-durometer polyurethane and the like. A third category includes balloons which include both elastic and inelastic portions. Within the category of elastic balloons, two sub-categories exist: a first sub-category wherein a combination of material properties and/or wall thickness can be combined to produce a balloon that exhibits a measurable pressure-threshold for inflation, i.e. the balloon becomes inflated only after a minimum fluidic pressure is applied to the interior of the balloon; and a second sub-category, wherein the balloon expands elastically until an elastic limit is reached which effectively restricts the balloon diameter to a maximum value. It will be understood that the individual properties of the balloons in each of these categories can be applied to one or more advantages in the specific embodiments disclosed herein, these properties integrated singly or in combination. By way of example only, one or more of the following configurations can be employed: a highly elastic balloon can be used to achieve a wide range of operating diameters during treatment, e.g. during operation a desired balloon diameter can be achieved by adjustment of a combination of fluid temperature and pressure; a substantially inelastic balloon or a balloon that reaches its elastic limit within a diameter approximating a target tissue diameter (e.g. a duodenal mucosal diameter) can be used to achieve a relatively constant operating diameter that will be substantially independent of operating pressure and temperature; a balloon with a pressure-threshold for inflation can be used to maintain an uninflated diameter during relatively low pressure conditions of fluid flow and then achieve a larger operating diameter at higher pressure conditions of flow. Pressure-thresholded balloons can be configured in numerous ways. In one embodiment, a balloon is configured to have a relatively thick wall in its uninflated state, such as to maximize an electrically and/or thermally insulating effect while the balloon is maintained in this uninflated state. The balloon can be further configured such that its wall thickness decreases during radial expansion (e.g. to decrease an electrically and/or thermally insulating effect). In another embodiment, a balloon is configured to have a relatively small diameter in its uninflated state (e.g. a diameter that is small relative to the inner diameter of tubular target tissue such as the diameter of the mucosal layer of duodenal wall tissue), such as to minimize or completely eliminate apposition between the balloon and the surrounding tissue to minimize heat, RF and/or other energy transfer into the surrounding tissue until the balloon is fully inflated. In another embodiment, a balloon and an ablation system or device are configured to circulate a flow of fluid through the balloon (e.g. an elastic balloon or an inelastic balloon) at a sufficiently low enough pressure to prevent apposition of the balloon or other device component with target tissue, such as to pre-heat one or more surfaces of the ablation system or ablation device that are in fluid communication with the balloon. In this configuration, when the balloon or other ablation element is positioned to deliver energy to target tissue, the temperature of the balloon or other ablation element will be at a desired level or it will rapidly and efficiently reach the desired level for treatment (i e minimal heat loss to the fluid path components due to the pre-heating or pre-cooling). These configurations provide a method of delivering energy to tissue with an ablative fluid filled balloon. A "thermal priming" procedure can be performed prior to one or more target tissue treatments, such as to improve thermal response time of one or more portions of the treatment device. Ablative fluid filled balloon treatment devices as well as thermal priming devices and methods can be configured as is described in applicant's co-pending International Patent Application Serial Number PCT/US2013/028082, entitled "Heat Ablation Systems, Devices and Methods for the Treatment of Tissue", filed Feb. 27, 2013, the contents of which is incorporated herein by reference in its entirety.

At times during treatment when it is desirable to initiate, increase and/or otherwise modify the treatment of tissue by one or more tissue treatment elements (e.g. a fluid delivery element delivering ablative fluid, a mechanically abrasive element, a hot or cold fluid balloon delivering a thermal dose and/or an electrode delivering RF energy), the treatment assembly diameter (e.g. the diameter of a balloon, deployable cage, expandable tube or other expandable assembly) can be increased in situ to move a treatment element closer to target tissue and/or to change the contact force between the treatment element and the target tissue. At times during treatment when it is desirable to stop or otherwise decrease the amount of tissue treatment, the treatment assembly diameter can be reduced in situ, such as to prevent or reduce delivery of energy or other treatment to the target tissue by eliminating or reducing tissue contact of one or more treatment elements (e.g. electrodes, abrasive surfaces or ablative fluid filled balloons). For those cases where the native diameter of the target tissue varies substantially within the treatment zone, then a highly elastic or compliant balloon or other expandable element can be employed, such as a balloon or deployable cage which can be adjusted to achieve a wide range of operating diameters.

Alternatively or additionally, to initiate, increase and/or otherwise modify the treatment of tissue by one or more treatment elements (e.g. a fluid delivery element delivering ablative fluid, a mechanically abrasive element, a hot or cold fluid balloon delivering a thermal dose and/or an electrode delivering RF energy), the diameter of the target tissue can be decreased in situ to move target tissue closer to a treatment element and/or to change the contact force between the target tissue and the treatment element. To stop or otherwise decrease ablation of tissue, the diameter of tissue neighboring a treatment element can be increased in situ, such as to prevent or reduce delivery of energy or other treatment to the target tissue by eliminating or reducing tissue contact of one or more treatment elements (e.g. electrodes, abrasive surfaces or ablative fluid filled balloons). The diameter of the tissue proximate a treatment element can be increased or decreased, independent of the treatment assembly diameter, by means of delivering and/or withdrawing a fluid, to and/or from a lumen surrounded by target tissue, such as by using standard gastrointestinal insufflation techniques. Typical insufflation fluids include but are not limited to: gases such as carbon dioxide or air; liquids such as water or saline solution; and combinations of these. The insufflation fluids can be introduced through a treatment device, through an endoscope such as an endoscope through which the treatment device is inserted, and/or via another device placed proximate the target tissue. Delivery of insufflation fluids can be performed to move target tissue away from one or more treatment elements, such as to stop transfer of energy to target tissue at the end of a treatment of target tissue as described hereabove. Alternatively or additionally, delivery of insufflation fluids can be performed to manipulate tissue, such as to distend and/or elongate tissue. Removal of these insufflation fluids and/or the application of a vacuum or other negative pressure can be used to decrease the diameter of the target tissue, such as to bring the target tissue in closer proximity to one or more treatment elements and/or to increase the contact force between target tissue and one or more treatment elements, also as described hereabove. In this tissue diameter controlled approach, a treatment assembly including a balloon that can be maintained at a substantially constant diameter can be desirable, such as a substantially inelastic balloon such as a balloon with an elastic-limit.

Referring now to FIG. 1, a schematic view of a system for ablating or otherwise treating target tissue is illustrated, consistent with the present inventive concepts. System 10 is configured to treat target tissue TT, such as to treat one or more patient diseases or disorders selected from the group consisting of: diabetes; obesity or otherwise being overweight; hypercholesterolemia; exercise intolerance; psoriasis; and combinations of these. In the embodiment of FIG. 1, target tissue TT includes one or more tissue portions within a body lumen of a mammalian patient as has been described hereabove. In some embodiments, target tissue TT comprises a continuous or discontinuous circumferential segment of a duodenum, such as a volume of tissue comprising at least 50% of the duodenal mucosa, or at least 67% of the duodenal mucosa. In some embodiments, target tissue TT comprises a treatment portion comprising duodenal mucosal tissue and a safety-margin portion comprising at least an innermost layer of the duodenal submucosa. System 10 can be configured to treat the duodenal mucosa while avoiding damage to duodenal adventitial tissue, such as by avoiding damage to tissue beyond the mucosa, to tissue beyond the superficial submucosa and/or to tissue beyond the deep submucosa.

System 10 can include one or more tissue treatment devices, such as first treatment device 100 and second treatment device 100'. First treatment device 100 can be used in a first clinical procedure including treatment of target tissue, and second treatment device 100' can be used in a second clinical procedure including treatment of target tissue, as is described in reference to FIG. 2 herebelow. In some embodiments, the second clinical procedure is performed at least twenty-four hours after the first clinical procedure. Target tissue treatments performed in the second clinical procedure can be constructed and arranged based on one or more outcomes of the first clinical procedure, also as is described below in reference to FIG. 2. Additional treatment devices can be included, such as to perform a third or other subsequent clinical procedures including target tissue treatments.

First treatment device 100 and second treatment device 100' can be similar or dissimilar treatment devices, and can be constructed and arranged to perform similar or dissimilar treatments to similar or dissimilar volumes of tissue. Differences between first treatment device 100 and second treatment device 100' can include but are not limited to: type of ablative treatment provided such as type of energy delivered; type of non-ablative treatment provided; configuration of a treatment assembly or a treatment element included such as configuration of a treatment assembly or a treatment element included in the treatment device; length of the device; diameter of a portion of the device; and combinations of these. In some embodiments, first treatment device 100 comprises a first treatment element constructed and arranged to deliver a different form of energy than a second treatment element of second treatment device 100'. Alternatively or additionally, first treatment device 100 can comprise a first treatment element with a different geometry (e.g. different diameter, length and/or tissue contact surface area or shape), than a second treatment element of second treatment device 100'.

In some embodiments, system 10 can be constructed and arranged as is described in applicant's co-pending International Patent Application Serial Number PCT/US2012/021739, entitled "Devices and Methods for the Treatment of Tissue", filed Jan. 18, 2012, the contents of which is incorporated by reference in its entirety. In some embodiments, first treatment device 100 and/or second treatment device 100' can be constructed and arranged to ablate tissue, such as with an ablation treatment selected from the group consisting of: delivery of thermal energy from a balloon filled with fluid at an ablative temperature; RF energy ablation; delivery of an ablative fluid directly to tissue; cryoablation; delivery of laser energy; delivery of sound energy such as subsonic sound energy or ultrasonic sound energy; and combinations of these.

System 10 can include one or more body introduction devices, such as endoscope 350. Endoscope 350 can comprise a standard gastrointestinal endoscope such as an endoscope with one or more working channels configured to slidingly receive first treatment device 100 (as shown) and/or second treatment device 100'.

System 10 can include energy delivery unit (EDU) 330, which can be operably attached to first treatment device 100 (as shown) and/or second treatment device 100'. EDU 330 can be configured to provide numerous forms of energy to one or more treatment elements of first treatment device 100 and/or second treatment device 100', such as an energy form selected from the group consisting of: RF energy; microwave energy; laser energy; sound energy such as subsonic sound energy or ultrasound energy; chemical energy; thermal energy such as heat energy or cryogenic energy; and combinations of these.

System 10 can include pumping assembly 340 which can provide and/or remove one or more fluids from one or more devices of system 10, such as first treatment device 100, second treatment device 100' and/or endoscope 350. Pumping assembly 340 can include one or more fluid reservoirs, such as fluid reservoir 341 shown, and/or it can receive or supply fluids to EDU 330. In some embodiments, pumping assembly 340 and/or EDU 330 recirculate one or more fluids through a device of system 10, such as to recirculate fluid through first treatment device 100, second treatment device 100' and/or endoscope 350.

System 10 can include motion transfer assembly 320, which can be constructed and arranged to rotate, translate and/or otherwise move one or more devices, assemblies and/or components of system 10, as is described in detail herebelow.

System 10 can include controller 310, which can be constructed and arranged to automatically and/or manually control one or more devices, assemblies and/or components of system 10, as is described in detail herebelow.

Ablation device 100 comprises treatment assembly 140. Treatment assembly 140 includes one or more elements constructed and arranged to ablate or otherwise treat tissue, such as treatment element 145 shown. Treatment element 145 can comprise one or more elements selected from the group consisting of: an electrical energy delivery element such as one or more electrodes constructed and arranged to deliver RF energy; a fluid delivery element such as a nozzle or permeable surface constructed and arranged to deliver ablative fluid directly to target tissue TT; a balloon such as a balloon constructed and arranged to receive an ablative fluid and deliver hot or cold thermal energy to ablate target tissue TT; a laser energy delivery element such as an optical fiber, a focusing lens and/or other optical component; a sound energy delivery element such as a piezo-based element configured to deliver ultrasonic and/or subsonic energy; a tissue abrading element; and combinations of these. Treatment element 145 can be positioned on, in, within and/or passing through one or more components of treatment assembly 140, such as a balloon, cage, spline or other component as are described in detail herein. In some embodiments, treatment assembly 140 and treatment element 145 are the same component, such as when treatment assembly 140 comprises a balloon constructed and arranged to receive hot or cold ablative fluid to treat target tissue.

In some embodiments, first treatment device 100 and/or second treatment device 100' delivers heat or thermal energy to tissue, such as when treatment assembly 140 and/or treatment element 145 comprises a balloon constructed and arranged to be filled with an ablative fluid comprising a hot or cold volume of fluid at a temperature sufficient to ablate tissue when the balloon contacts the tissue. The hot or cold volume of fluid can be provided to treatment assembly 140 and/or treatment element 145 via EDU 330 and/or pumping assembly 340. System 10 can be configured to deliver thermal energy to tissue as is described in applicant's co-pending International Patent Application Serial Number PCT/US2013/02802, entitled "Heat Ablation Systems, Devices and Methods for the Treatment of Tissue", filed Feb. 27, 2013, the contents of which is incorporated herein by reference in its entirety.

In some embodiments, first treatment device 100 and/or treatment device 100' delivers RF energy to tissue, such as when treatment element 145 comprises one or more electrodes constructed and arranged to receive RF energy provided by EDU 330. In some embodiments, EDU 330 is configured to deliver RF energy to one or more electrodes of first treatment device 100 and/or second treatment device 100', such as in a monopolar mode through a grounding pad such as ground pad 70 and/or in a bipolar mode between two or more electrodes of first treatment device 100 or second treatment device 100'. System 10 can be configured to deliver RF energy to tissue as is described in applicant's co-pending International Patent Application Serial Number PCT/US2013/052786, entitled "Electrical Energy Ablation Systems, Devices and Methods for the Treatment of Tissue", filed Jul. 30, 2013, the contents of which is incorporated herein by reference in its entirety.

In some embodiments, first treatment device 100 and/or second treatment device 100' delivers ablative fluid directly to tissue, such as when treatment element 145 comprises one or more fluid delivery elements. In these embodiments, treatment element 145 can be constructed and arranged to ablate target tissue TT by delivering ablative fluid provided by EDU 330 and/or pumping assembly 340. Treatment element 145 can include one or more fluid delivery elements selected from the group consisting of: nozzle such as a nozzle configured to deliver a cone or other shaped spray of fluid; opening; hole; slit; permeable membrane; misting element; vaporizer; and combinations of these. Ablative fluid can comprise one or more liquids or gases that are delivered to target tissue TT at a temperature above or below a threshold that would ablate tissue. In some embodiments, the ablative fluid delivered by treatment element 145 comprises steam, such as steam at a temperature of 100° C. or above. In some embodiments, the ablative fluid delivered by treatment element 145 comprises a vaporized fluid at a temperature below 100° C., such as a vaporized fluid at a temperature between 70° C. and 90° C. In some embodiments, the ablative fluid delivered by treatment element 145 comprises a gas, such as a gas between 60° C. and 99° C., such as a gas delivered to tissue at a temperature between 70° C. and 90° C. In some embodiments, the ablative fluid delivered by treatment element 145 comprises a vaporized liquid, such as a vaporized liquid delivered to tissue at a temperature below 100° C., such as at a temperature between 70° C. and 90° C. Alternatively or additionally, an ablative fluid delivered by treatment element 145 can comprise one or more liquids or gases that cause tissue necrosis or otherwise treat target tissue TT as has been described hereabove, using one or more chemically active agents (e.g. ablation not primarily caused by delivery or removal of heat from tissue). In these embodiments, the agent can comprise an agent selected from the group consisting of: sclerotic agent; acid; base; saline; alcohol; carbon dioxide; nitrous oxide; nitrogen; acetic acid; glycerol; and combinations of these. In these embodiments, a counter-acting agent can be included, such as a counter-acting agent delivered by treatment device 100 or another device or component of system 10 that is used to neutralize, impede, reduce and/or limit tissue ablation caused by the delivery of a necrotic agent-based ablative fluid. The counter-acting agent can be delivered by treatment element 145 or another component. The counter-acting agent can comprise an agent selected from the group consisting of: anti-sclerotic agent; base; acid; buffer solution; saline; water; and combinations of these. System 10 can be configured to deliver ablative fluid directly to tissue as is described in applicant's co-pending International Patent Application Serial Number PCT/US2013/054219, entitled "Ablation Systems, Device and Methods for the Treatment of Tissue", filed Aug. 8, 2013, the contents of which are incorporated herein by reference in their entirety.

As shown in FIG. 1, first treatment device 100 includes coaxial shafts 111a and 111b. Shaft 111b has a distal end 112. Shafts 111a and 111b are sized and configured such that shaft 111a slidingly receives shaft 111b, such that they can be advanced and/or retracted in unison or independently. Alternatively, first treatment device 100 can comprise a single shaft. In some embodiments, device 100 comprises a flexible portion (e.g. a portion of shafts 111a and 111b including distal end 112) with a diameter less than 6 mm. In some embodiments, the flexible portion is configured to pass through a working channel of an endoscope with a diameter of less than or equal to 6.0 mm, 4.2 mm, 3.8 mm, 3.2 mm or 2.8 mm. In some embodiments, device 100 comprises a shaft length of 100 cm or longer, or otherwise comprises a length sufficient to be orally and/or nasally inserted into a patient, and subsequently advanced to reach the esophagus, stomach, duodenum, jejunum; and/or rectally inserted into a patient, and subsequently advanced to reach the terminal ileum of that patient. In FIG. 1, shafts 111a and 111b have been inserted through a working channel (e.g. a 6 mm working channel), lumen 351, of endoscope 350, typically a gastrointestinal endoscope. Shafts 111a and/or 111b can be inserted over a standard interventional guidewire, such as guidewire 60 shown exiting distal end 112 of shaft 111b. In an alternative embodiment, shafts 111a and 111b are positioned in a side-by-side configuration, such as to be placed in two separate lumens of endoscope 350 or in two other non-coaxial locations. In some embodiments, one or both of shafts 111a or 111b passes through a body lumen or other internal body location alongside endoscope 350 (i.e. not through lumen 351, traveling relatively parallel with but external to endoscope 350). Shaft 111a and/or 111b can include manipulation means configured to deflect and/or steer a distal portion of the shaft, such as via one or more proximal handle controlled pull wires that extend and are attached to the distal portion of the shaft (handle and pull wires not shown but well known to those of skill in the art).

Treatment assembly 140 can be positioned on shaft 111a as shown. Treatment delivery element 145 is electrically, fluidly, mechanically and/or otherwise operably connected to conduit 141. Conduit 141 comprises one or more elongate filaments selected from the group consisting of: a wire such as one or more wires configured to deliver electrical or other power and/or transmit electrical or other data signals; an optical fiber such as one or more optical fibers configured to deliver power and/or transmit data signals; a tube such as a fluid delivery tube; a control rod such as an advanceable and/or retractable control rod; and combinations of these. Conduit 141 travels proximally through shaft 111a and operably attaches to EDU 330, pumping assembly 340, motion transfer assembly 320 and/or another component, assembly or device of system 10.

In some embodiments, conduit 141 comprises one or more fluid delivery tubes constructed and arranged to deliver and/or recirculate heated or chilled fluid into treatment assembly 140, such as heated or chilled fluid received from EDU 330 and/or pumping assembly 340 and delivered into treatment element 145, such as when treatment element 145 comprises a balloon or other fluid reservoir configured to receive ablative fluid at a temperature sufficient to ablate tissue when treatment element 145 contacts the tissue. Alternatively or additionally, conduit 141 can comprise one or more fluid delivery tubes constructed and arranged to deliver an ablative fluid to treatment assembly 140, such as ablative fluid provided by EDU 330 and/or pumping assembly 340 and delivered directly to target tissue TT by one or more treatment elements 145, such as when treatment element 145 comprises a fluid delivery element such as a nozzle. Conduit 141 can further comprise one or more insulating layers configured to prevent transfer of heat into and/or out of conduit 141. Conduit 141 can include a surrounding lumen which receives a circulating fluid configured to provide an insulating, warming and/or cooling effect on conduit 141 and/or any fluid contained within conduit 141. Conduit 141 and/or another fluid delivery tube of system 10 can comprise one or more elongate hollow tubes, such as a hollow tube positioned within shaft 111a. Alternatively, conduit 141 and/or another fluid delivery tube of system 10 can comprise a lumen within a shaft, such as a lumen within shaft 111a. In some embodiments, conduit 141 and/or another fluid delivery tube of system 10 comprises both a lumen and a hollow tube, such as when the lumen and hollow tube are fluidly connected in an end-to-end configuration. Conduit 141 typically attaches to EDU 330 and/or pumping assembly 340 with one or more operator attachable fluid connections ports, such as a fluid connection port included in a handle positioned on the proximal end of shaft 111a, handle not shown. Conduit 141 can comprise one or more fluid delivery tubes including one or more valves, not shown but such as a duck-bill or other valve used to regulate flow within conduit 141, such as to regulate flow pressure and/or direction.

In some embodiments, conduit 141 comprises one or more elongate filaments constructed and arranged to transmit energy and/or data. Conduit 141 can comprise one or more wires constructed and arranged to deliver RF energy to one or more electrode-type treatment elements 145, such as when the treatment elements 145 are configured to ablate target tissue TT in monopolar and/or bipolar modes as described herein. Conduit 141 can comprise one or more filaments constructed and arranged to deliver laser energy, such as one or more optical fibers constructed and arranged to deliver laser energy to one or more lenses or other optical component-type treatment elements 145, such as to ablate target tissue TT with laser or other light energy. Conduit 141 can comprise one or more wires or other energy transfer filaments constructed and arranged to allow a sound producing-type treatment element to ablate target tissue TT with sound energy such as ultrasonic or subsonic sound energy. Conduit 141 can comprise one or more wires or optical fibers configured to transmit information, such as information received from a sensor of system 10 as described herebelow.

In some embodiments, conduit 141 comprises one or more control rods constructed and arranged to cause one or more treatment elements 145 to rotate and/or translate, such as when conduit 141 is operably attached to motion transfer assembly 320. In some embodiments, one or more treatment elements 145 comprise a surface configured to abrade or otherwise disrupt tissue as it is rotated and/or translated by movement of conduit 141. Alternatively or additionally, one or more treatment elements 145 can deliver energy and/or fluid to tissue, and movement of one or more control rods of conduit 141 changes the location of the tissue portion receiving the energy and/or fluid. Motion of one or more treatment elements 145 can be configured to treat a full circumferential (i.e. 360°) segment of tubular tissue, or a partial circumferential (e.g. a 45°-350°) segment of tubular tissue. Motion of one or more treatment elements 145 can be configured to treat a particular axial length of tubular tissue, such as a length comprising at least 25% of the length of the duodenum, or at least 35% of the length of the duodenum, or at least 50% of the length of the duodenum, or at least 66% of the length of the duodenum; or at least 75% of the length of the duodenum.

Treatment assembly 140 can be radially expandable, similar to expandable assembly 130 described herebelow. System 10 can be configured to allow expansion of treatment assembly 140 to cause one or more treatment elements 145 to contact a tissue wall such as a duodenal wall, such as when one or more treatment elements 145 comprise a balloon configured to ablate tissue with a contained hot or cold fluid, or when one or more treatment elements 145 comprise an electrode configured to deliver RF energy to ablate tissue. Treatment assembly 140 can be configured to expand to a diameter less than the diameter of the target tissue TT, such as when a vacuum is applied to cause the target tissue TT diameter to decrease to make contact with one or more treatment elements 145, as has been described hereabove. System 10 can be configured to allow expansion of treatment assembly 140 to cause one or more treatment elements 145 to be positioned at a fixed distance from the luminal wall of tubular tissue, such as a positioning at a fixed distance of at least 250 microns, at least 500 microns, or at least 1 mm from a tissue wall, such as when one or more treatment elements 145 are configured to deliver ablative fluid to the target tissue TT and/or to deliver light energy to the target tissue TT. In addition to treating target tissue TT, treatment assembly 140 and/or one or more treatment elements 145 can be configured in one or more various forms to modify, manipulate, measure and/or diagnose target tissue TT and/or other tubular or non-tubular tissue.

In some embodiments, treatment element 145 can be further configured to extract fluids, such as to extract previously administered ablative fluids and/or insufflation fluids from a body lumen. Fluid extraction can be performed prior to, during and/or after treatment of target tissue TT.

EDU 330 and/or pumping assembly 340 can comprise multiple heat or cold sources used to modify the temperature of one or more fluids provided by and/or passing through EDU 330 and/or pumping assembly 340. The heat or cold sources can be at a fixed temperature or they can be variable. In some embodiments, a first heat or cold source is at a fixed temperature and a second heat or cold source is at a variable temperature.

In some embodiments, a cooling fluid is delivered, prior to, during and/or after the treatment of target tissue TT, such as to precisely control target tissue ablation and avoid ablation of non-target tissue. The cooling fluid can be provided by EDU 330 and/or pumping assembly 340, and it can be delivered to tissue, such as target or non-target tissue, and/or it can be delivered to a component of system 10 such as to reduce the temperature of a component of treatment assembly 140. Treatment element 145 and/or another component of system 10 can be constructed and arranged to deliver the cooling fluid to one or more tissue surfaces, such as a cooling fluid delivered to treatment element 145 via conduit 141 and configured to reduce the temperature of one or more volumes of tissue. The ablation provided by system 10 can comprise a non-desiccating or a desiccating ablation. In some embodiments, a non-desiccating ablation is performed for a first portion of target tissue TT such as in a first tissue treatment, and a desiccating ablation is performed for a second portion of target tissue TT such as in a second tissue treatment. Non-desiccating ablations can be performed to treat over-lapping portions of target tissue TT, and/or to avoid creation of tissue debris if desired. Desiccating ablations can be performed to achieve a higher thermal gradient, to remove excess tissue, and/or to ablate rapidly if desired.

EDU 330 and/or pumping assembly 340 can be configured to deliver a hot fluid to pre-heat one or more components of system 10. In some embodiments, the one or more components include conduit 141; a fluid delivery tube such as a tube within shaft 111*a*, a fluid delivery lumen such as a lumen within shaft 111*a*; shaft 111*b*; treatment element 145; and combinations of these. System 10 can be configured to pre-heat one or more components by circulating or recirculating hot fluid, such as a hot liquid or gas. In some embodiments, treatment assembly 140 contains and/or treatment element 145 delivers a hot fluid, and one or more components of system 10 are pre-treated with a hot gas. Alternatively or additionally, system 10 can comprise one or more insulators surrounding one or more conduits, lumens and/or shafts of treatment device 100 and/or system 10, such as an insulator surrounding conduit 141 and configured to prevent transfer of heat across (e.g. into or out of) conduit 141.

System 10 can be configured to maintain target tissue TT or other tissue below a threshold or within a temperature range, such as in a closed-loop configuration through the use of one or more sensors such as sensor 149 of treatment assembly 140 or sensor 139 of expandable assembly 130, each described in detail herebelow. In some embodiments, tissue temperature is maintained below 100° C., such as between 60° C. and 90° C., such as between 65° C. and 85° C. In some embodiments, system 10 is configured to maintain the temperature of target tissue TT at a setpoint temperature. The setpoint temperature can vary over time. System 10 can be configured to deliver energy at a level that increases and/or decreases over time. In some embodiments, treatment assembly 140 is constructed and arranged to cause the temperature of at least a portion of target tissue TT to rapidly rise to a setpoint (e.g. a setpoint between 60° C. and 75° C.). After the target tissue TT reaches the setpoint temperature, system 10 can deliver energy or otherwise treat the target tissue TT to maintain the setpoint temperature for an extended time period.

In some embodiments, EDU 330 and/or pumping assembly 340 is configured to heat or chill one or more fluids, such as one or more ablative fluids 331 or other fluids. In some embodiments, treatment assembly 140 is configured to heat or chill one or more fluids. Applicable heating and cooling elements include but are not limited to: heat exchangers, heating coils, pettier components, refrigeration assemblies, gas expansion coolers, and the like. Heating and cooling can be applied to a source of fluid (e.g. fluid reservoir 341), or to fluid that is withdrawn from device 100 (e.g. a recirculating fluid and/or a body extracted fluid such as recovered, previously delivered, ablative or insufflating fluid). EDU 330 and/or pumping assembly 340 can include one or more pumps configured to deliver and/or extract fluid at a particular flow rate, pressure, or other fluid delivery parameter. System 10 can be configured to deliver fluid at a sufficiently high temperature to ablate target tissue TT, after which a cooling fluid is delivered to removal thermal energy from target tissue TT and/or other tissue, such as cooling fluid delivered for a time period of at least 2 seconds, at least 5 seconds, at least 10 seconds or at least 20 seconds.

In some embodiments, treatment device 100 further includes a radially expandable assembly, expandable assembly 130, mounted to shaft 111*b*. In some embodiments, treatment device 100 comprises a single shaft, and both treatment assembly 140 and expandable assembly 130 are mounted to that single shaft. Expandable assembly 130 can be configured in one or more various forms to treat, modify, manipulate, measure and/or diagnose target tissue TT and/or other tubular tissue. Expandable assembly 130 can comprise one or more expandable elements 131, such as one or more expandable elements selected from the group consisting of: an inflatable balloon; a radially expandable stent or cage; an array of splines; one or more radially deployable arms; a spiral or other helical structure; a furlable structure such as a furlable sheet; an unfurlable structure such as an unfurlable sheet; a foldable structure such as a foldable sheet; an unfoldable structure such as an unfoldable sheet; and combinations of these. In some embodiments, expandable assembly 130 is inflatable (e.g. an inflatable balloon), and inflation fluid can be delivered into expandable assembly 130 via an inflation tube 136. Inflation tube 136 can comprise a lumen of shaft 111b (or a tube within shaft 111b) that travels proximally through shaft 111b and shaft 111a, such as to receive inflation fluid delivered by pumping assembly 340. Expandable assembly 130 can be positioned distal to treatment assembly 140 as shown in FIG. 1, or alternatively, expandable assembly 130 can be positioned proximal to treatment assembly 140, such as when treatment assembly 140 is mounted to shaft 111b and expandable assembly 130 is mounted to shaft 111a.

Expandable assembly 130 can be configured to seal a body lumen location, such as to create a full or partial occlusive barrier at a location within the duodenum or other location in the gastrointestinal tract. System 10 can be configured to cause a fluid or other seal comprising an occlusive barrier selected from the group consisting of: a pressure seal; a cryogenically applied seal such as an ice ball seal; a vacuum seal; a full circumferential seal; a partial circumferential seal; and combinations of these. In some embodiments, treatment element 145 treats a portion of target tissue TT located proximal or distal to the occlusive barrier. System 10 can include multiple expandable assemblies configured to seal a body lumen location, such as first expandable assembly which provides a seal at a proximal end of a segment of tubular tissue, and a second expandable assembly which provides a seal at a distal end of the tubular tissue segment. In some embodiments, treatment element 145 treats a portion of target tissue TT located between the two sealed locations, such as between two locations of the duodenum, each duodenal location sealed by an expandable component or assembly of device 100. One or more expandable assemblies can be configured to occlude a first location of a body lumen, followed by subsequent occlusions of one or more different locations within the body lumen. System 10 can be configured to apply a vacuum between two occlusive elements, such as a vacuum applied by one or more treatment elements 145, via one or more functional elements 138 and/or 148 (attached to expandable assembly 130 and treatment assembly 140, respectively, each functional element described in detail herebelow) and/or by another device or component of system 10. Applied vacuum can be used to modify (e g change the shape of) the tubular tissue between the two occlusive elements and/or to increase the sealing force and/or the circumferentiality of the seal. In some embodiments, system 10 is configured to deploy a detached-balloon configured to occlude a body lumen, where the detached-balloon can later be punctured or otherwise deflated for physiologic removal by the gastrointestinal tract. Deployed balloons or other occlusive elements of system 10 can be positioned to protect tissue, such as to protect the ampulla of Vater and/or the pylorus from adverse effects that can be caused by treatment of target tissue TT by treatment element 145.

In some embodiments, in addition to expandable assembly 130, treatment assembly 140 can be radially expandable and/or include one or more radially expandable elements, such as those described hereabove in reference to expandable assembly 130. In some embodiments, treatment assembly 140 is configured to radially expand and cause treatment element 145 to move closer to and/or become in contact with target tissue TT. Expansion of treatment assembly 140 can occur prior to, during and/or after treatment of target tissue TT by treatment element 145. Treatment element 145 can be mounted on, within and/or inside of an expandable assembly, such as on, within and/or inside of an expandable balloon.

In some embodiments, expandable assembly 130 and/or treatment assembly 140 comprise a length of at least 10 mm, such as a length between 10 mm and 40 mm, a length between 15 mm and 30 mm, or a length between 20 mm and 25 mm. In some embodiments, expandable assembly 130 and/or treatment assembly 140 comprise a length less than or equal to 15 mm, such as when configured to treat curvilinear portions of the gastrointestinal tract. Multiple assemblies positioned on shafts 111a and/or 111b (e.g. between two and twenty treatment and/or expandable assemblies), such as expandable assembly 130 and treatment assembly 140, can be separated along a shaft by a distance less than or equal to 25 mm, such as a distance less than or equal to 20 mm. This separation distance can comprise the distance between a distal end of a tissue contacting portion of a first expandable element, and the neighboring proximal end of a tissue contacting portion of a second expandable element. In some embodiments, expandable assembly 130 comprises a length, and the separation distance between expandable assembly 130 and treatment assembly 140 is less than or equal to the expandable assembly 130 length. In these embodiments, treatment assembly 140 can comprise a similar length to that of expandable assembly 130, such as when both expandable assembly 130 and treatment assembly 140 comprise an ablation element as is described herebelow.

Expandable assembly 130 can include one or more fluid delivery elements, such as fluid delivery element 132 and/or fluid delivery element 135. Fluid delivery elements 132 and 135 are connected to one or more fluid delivery tubes (e.g. independent fluid delivery tubes), not shown but traveling proximally within shafts 111b and/or 111a and fluidly connected to EDU 330 and/or pumping assembly 340, such as via one or more ports on a handle of treatment device 100. Fluid delivery elements 132 and/or 135 can be rotatable, advanceable and/or retractable, such as via one or more control shafts, not shown but operably connected to motion transfer assembly 320. Fluid delivery elements 132 and/or 135 can comprise a nozzle or other fluid delivery element as described herein. Fluid delivery element 132 can be oriented such that fluid delivered through fluid delivery element 132 is directed toward one or more device 100 components or assemblies, such as toward treatment assembly 140 and treatment element 145 as shown in FIG. 1. Fluid delivery element 132 can be used to perform various functions such as the washing or removing of material from a device 100 component, or to cool or warm the temperature of a device 100 component. Fluid delivery element 135 can be directed toward or otherwise deliver fluid to tissue proximate device 100. Fluid delivery element 135 can have its distal end positioned within tissue (e.g. after an advancement), as shown in FIG. 1, such as to deliver fluid to one or more internal tissue layers. Alternatively, fluid delivery element 135 can have its distal end positioned in a body lumen, such as to deliver fluid to at least initially contact a tissue surface such as the wall of the duodenum. Fluid delivery element 135 can be configured to deliver a fluid to expand tissue, such as to expand sub-mucosal or other tissue as is described in applicant's co-pending International PCT Application Serial Number PCT/US2013/037485, entitled "Tissue Expansion Devices, Systems and Methods", filed Apr. 19, 2012, the contents of which is incorporated herein by reference in its entirety. Alternatively or additionally, a separate submucosal or other tissue expansion device can be included, such as tissue expansion device 200. Fluid delivery element 135 can be configured to deliver a cooling or warming fluid to tissue, and/or deliver a fluid configured to counter-act a chemically caused ablation, as has been described hereabove.

Expandable assembly 130 and/or treatment assembly 140 can be configured to expand to a diameter of at least 15 mm, such as a diameter of at least 20 mm, 25 mm or at least 30 mm Expandable assembly 130 and/or treatment assembly 140 can be resiliently biased, such as in a radially expanded or radially compacted state. Expandable assembly 130 and/or treatment assembly 140 can be expanded and/or compacted by a control shaft. Expandable assembly 130 and/or treatment assembly 140 can be configured to achieve a round or non-round shape (e.g. a football shape) when expanded. Expandable assembly 130 and/or treatment assembly 140 can approximate a tubular shape when expanded, such as a unidiameter or varying diameter tube shape. Expandable assembly 130 and/or treatment assembly 140 can be configured to un-fold to a radially expanded state, or to fold to a radially compacted state.

Expandable assembly 130 can comprise at least one functional element 138, and treatment assembly 140 can comprise at least one functional element 148. Functional elements 138 and/or 148 can be elements selected from the group consisting of: an ablation element such as one or more electrodes configured to deliver electrical energy such as radiofrequency (RF) energy; a sensor; a transducer; a fluid delivery element such as a needle, a fluid jet, a permeable membrane and/or an exit port; a heating element; a cooling element; and combinations of these.

In some embodiments, expandable assembly 130 is configured to ablate tissue, such as via functional element 138. Functional element 138 of expandable assembly 130 can comprise one or more ablation elements, such as those described in applicant's co-pending International PCT Application Serial Number PCT/US12/21739, entitled "Devices and Methods for the Treatment of Tissue", filed Jan. 18, 2012, the contents of which is incorporated herein by reference in its entirety. In some embodiments, functional element 138 comprises an ablation element selected from the group consisting of: an RF energy delivery element such as one or more electrodes, each comprising one or more elongate conductors; an ultrasonic transducer such as one or more piezo crystals configured to ablate tissue; a laser energy delivery element such as one or more optical fibers and/or laser diodes; a heat delivery element such as a hot fluid filled balloon; a rotating ablation element; a circumferential array of ablation elements; and combinations of these. In these embodiments, either or both expandable assembly 130 or treatment assembly 140 can be used to ablate target tissue TT. EDU 330 or another component of system 10 can be configured to deliver RF or other energy to functional element 138. System 10 can include ground pad 70, such as a standard RF energy delivery ground pad typically placed on the patient's back, such that EDU 330 can supply RF energy to functional element 138 and/or any other electrodes of system 10 in monopolar, bipolar and/or combined monopolar-bipolar energy delivery modes.

In some embodiments, expandable assembly 130 is configured to perform at least one non-ablative function. Expandable assembly 130 can be configured to occlude or partially occlude a lumen surrounded by tissue (as described hereabove), such as a lumen of the gastrointestinal tract to be occluded during an insufflation procedure. Expandable assembly 130 can be configured to manipulate tissue, such as to linearize and/or distend gastrointestinal tissue by frictionally engaging (e.g. when expanded) and applying forces to the tissue (e.g. by advancing and/or retracting shaft 111b). In some embodiments, one or more expandable assemblies 130 can perform a function selected from the group consisting of: linearizing curvilinear tissue; distending tissue; expanding tissue; occluding a body lumen; and combinations of these. Expandable assembly 130 can be configured to test and/or diagnose tissue, such as when expandable assembly 130 is used to measure a diameter of tubular tissue into which it has been inserted. Diameter measurements can be performed in various ways, including but not limited to: injection of a radiopaque fluid into assembly 130 and fluoroscopic measurement of the injected fluid; controlled inflation of assembly 130 to a pressure whose level corresponds to a luminal diameter; and combinations of these. In some embodiments, device 100 includes an expandable assembly that can be expanded with one or more control rods (not shown), such as to perform a diametric measurement of tubular tissue by precision measurement of control rod advancement (e.g. when control rod position correlates to expandable assembly diameter). Alternatively or additionally, tubular tissue diameter can be determined by measuring the diameter of an expandable assembly when it initially, circumferentially contacts the wall of tubular tissue (e.g. when a specific radial force is achieved and/or when contact is observed such as using fluoroscopy or ultrasound visualization devices). In some embodiments, system 10 includes a separate device, such as a balloon catheter, used to perform a diameter measurement. One or more energy delivery or other ablation parameters can be adjusted based on the measured diameter of target tissue TT and/or a target tissue portion.

In some embodiments, expandable assembly 130 is configured to expand or otherwise modify one or more layers of tissue, such as when fluid delivery element 135 and/or functional element 138 comprises a needle and/or water jet configured to expand submucosal tissue of the gastrointestinal tract, as has been described hereabove. Alternatively or additionally, system 10 can include a separate tissue expansion device, tissue expansion device 200. Tissue expansion can greatly alleviate the need for precision of treatment, such as precision of delivery of energy and/or precision of delivery of an ablative fluid, due to the increased size (e.g. increased depth) of the target tissue TT including an associated safety-margin of tissue to which treatment causes no significant adverse event (e.g. an expanded submucosal layer prior to a mucosal layer ablation).

In some embodiments, expandable assembly 130 and/or treatment assembly 140 comprise a shape that can be adjusted by an operator, such as via a control rod manipulatable at a proximal handle and/or by motion transfer assembly 320. In some embodiments, the shape of the arrangement of one or more treatment elements 145 can be operator modified by adjusting the shape of treatment assembly 140.

Treatment element 145 can be configured to treat various thicknesses of gastrointestinal tissue, such as at least the innermost 500 microns of duodenal tissue, or at least the innermost 1 mm of duodenal tissue. In some embodiments, treatment element 145 can be configured to ablate or otherwise treat a thickness of at least 600 microns, at least 1 mm or at least 1.25 mm, such as when treating the mucosa of the stomach. Treatment element 145 can be configured to treat a volume of tissue comprising a surface area and a depth, where the ratio of magnitude of the depth to the magnitude of the surface area is less than or equal to 1 to 100 (e.g. less than 1%), or less than or equal to 1 to 1000 (e.g. less than 0.1%). In some embodiments, expandable assembly 130 and/or treatment assembly 140 are configured to be in a relatively rigid state, such as during treatment of target tissue TT.

Treatment element 145 and/or other treatment elements of the present inventive concepts can be arranged in an array of elements, such as a circumferential or linear array of elements. The circumferential array can comprise a partial circumferential array of treatment elements 145, such as an array covering approximately 45° to 300° of circumferential area. Partial circumferential arrays of treatment elements 145 can treat a first target tissue portion and a second target tissue portion in two sequential steps, where the array is rotated between treatments (e.g. energy deliveries). The circumferential array can comprise a full 360° array of treatment elements 145, such that a full circumferential volume of target tissue TT can be treated in a single or multiple treatments (e.g. energy deliveries) that do not require repositioning of treatment assembly 140. In some embodiments, less than 360° of tubular tissue is treated, such as by treating a circumferential portion of tissue comprising less than or equal to a 350°, or between 300° and 350°, such as to prevent a full circumferential scar from being created.

Two or more treatment elements 145 can be arranged in a helical array. In some embodiments, at least three, four or five treatment elements independently treat target tissue, in similar or dissimilar treatments (e.g. similar or dissimilar amounts of energy, provided simultaneously and/or sequentially by EDU 330).

In some embodiments, EDU 330 and/or another device or component of system 10 provides electrical or other energy to a component of treatment device 100, such as electrical energy provided to a heating coil in a distal portion of device 100, not shown but typically connected to one or more wires traveling proximally through shaft 111a. EDU 330 and/or another device or component of system 10 can provide energy such as electrical energy to one or more of functional element 138 and/or functional element 148 such as when either comprises a transducer or other powered component.

Treatment element 145 can comprise one or more treatment elements configured to treat substantially the entire length of the duodenum simultaneously and/or without having to reposition treatment device 100, such as when treatment element 145 comprises an array of treatment elements positioned along substantially the entire length of the target tissue, or when treatment element 145 comprises at least one treatment element configured to rotate and/or translate along substantially the entire length of target tissue. Treatment element 145 and/or other tissue treatment elements of the present inventive concepts can be configured to treat at least 25% of the entire length of the duodenum simultaneously and/or without having to reposition treatment device 100. Treatment element 145 and/or other ablation elements of the present inventive concepts can be configured to treat a first portion of target tissue TT followed by a second portion of target issue TT. The first and second treated tissue portions can be overlapping and they can have non-parallel central axes (e.g. tissue portions in a curved portion of the duodenum). Three or more target tissue portions can be treated, such as to cumulatively ablate at least 25% or at least 50% of the duodenal mucosa.

In some embodiments, expandable assembly 130 and/or treatment assembly 140 comprise inflatable or otherwise expandable balloons, such as one or more of: a compliant balloon; a non-compliant balloon; a balloon with a pressure threshold; a balloon with compliant and non-compliant portions; a balloon with a fluid entry port; a balloon with a fluid exit port; and combinations of these. In some embodiments, expandable assembly 130 and/or treatment assembly 140 comprise a balloon which is fluidly attached to an inflation tube, such as inflation tube 136 which travels proximally through shaft 111a and/or 111b and is attached to an inflation port, not shown but typically attached to a handle on the proximal end of treatment device 100.

In some embodiments, functional element 138 of expandable assembly 130 comprises an abrasive element configured for abrading target tissue, such as an abrasive element attached to a balloon or expandable cage.

Shafts 111a and 111b can include one or more lumens passing therethrough, and can comprise wires and/or optical fibers for transfer of data and/or energy such as RF energy to functional element 138 and/or 148. Shafts 111b and/or 111a can comprise one or more shafts, such as one or more concentric shafts configured to deliver and/or recirculate hot and/or cold fluid through expandable assembly 130 and/or treatment assembly 140, respectively. In some embodiments, a heated fluid is used to pre-heat one or more treatment device 100 components and/or to deliver a bolus of hot fluid energy, each as described in applicant's co-pending International PCT Application Serial Number PCT/US2013/028082, entitled "Heat Ablation Systems, Devices and Methods for the Treatment of Tissue", filed Feb. 27, 2013, the contents of which is incorporated herein by reference in its entirety. Device 100 can comprise multiple expandable assemblies 130, such as a first expandable assembly positioned proximal to treatment assembly 140 (not shown) and a second expandable assembly positioned distal to treatment assembly 140 (assembly 130 as shown in FIG. 1).

Figure 3:
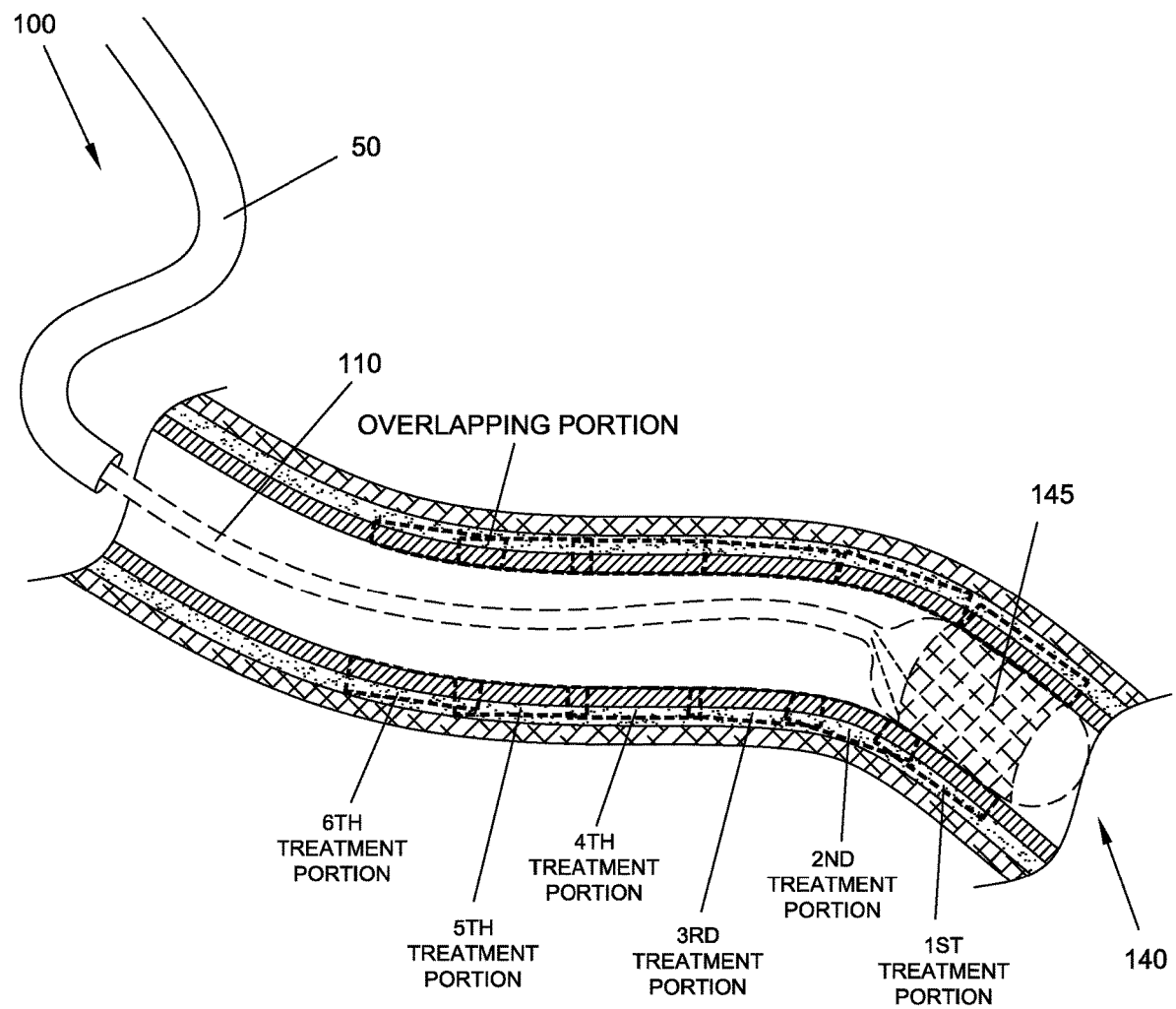
FIG. 3 is a side sectional view of the distal portion of a treatment device inserted into a curvilinear section of duodenum, consistent with the present inventive concepts.

Treatment assembly 140 and/or expandable assembly 130 can be configured to ablate tissue or otherwise perform a function while positioned in a curved segment of the gastrointestinal tract, such as is described in reference to FIG. 3 herebelow.

System 10 can be configured to ablate or otherwise treat target tissue TT, such as duodenal mucosal tissue, while avoiding damaging non-target tissue, such as the gastrointestinal adventitia. Target tissue TT can include at least a portion of safety-margin tissue comprising tissue whose ablation causes minimal or no adverse effect to the patient, such as sub-mucosal tissue of the gastrointestinal tract. Target tissue TT can comprise one or more portions of tissue that are treated simultaneously or sequentially. In some embodiments, the target tissue TT comprises the majority of the length of the duodenal mucosa, such as at least 25% or at least 50% of the duodenal mucosa. In some embodiments, the target tissue TT comprises at least 90% of the duodenal mucosa, or at least 95% of the duodenal mucosa. In some embodiments, the target tissue TT includes the full mucosal thickness of at least a portion of duodenal tissue, as well as at least the innermost 100 microns of submucosal duodenal tissue, or at least the innermost 200 microns of submucosal duodenal tissue. The target tissue TT can include at least one of ileal mucosal tissue or gastric mucosal tissue.

Endoscope 350 can be a standard endoscope, such as a standard gastrointestinal endoscope, or a customized endoscope, such as an endoscope including sensor 353 configured to provide information related to the tissue treatment of the present inventive concepts. Endoscope 350 can include camera 352, such as a visible light, ultrasound and/or other visualization device used by the operator of system 10 prior to, during and/or after the treatment of target tissue TT, such as during insertion and/or removal of endoscope 350 and/or shafts 111a and 111b of treatment device 100. Camera 352 can provide direct visualization of internal body spaces and tissue, such as the internal organs of the gastrointestinal tract. Endoscope 350 can be coupled with or otherwise include a guidewire, e.g. guidewire 60, such as to allow insertion of endoscope 350 into the jejunum and/or advancement of treatment device 100.

System 10 can be constructed and arranged to perform insufflation of a body lumen, such as insufflation of a segment of the gastrointestinal tract. The body lumen can be pressurized, such as by using one or more standard insufflation techniques. Insufflation fluid can be introduced through second lumen 354 of endoscope 350. Second lumen 354 travels proximally and connects to a source of insufflation liquid and/or gas, such as pumping assembly 340, and typically a source of air, carbon dioxide, water and/or saline. Alternatively or additionally, insufflation fluid can be delivered by treatment device 100, such as through shaft 111a and/or 111b, and/or through a port in expandable assembly 130 and/or treatment assembly 140, such as when functional elements 138 and/or 148, respectively, comprise a fluid delivery port attached to a source of insufflation liquid and/or gas (e.g. provided by pumping assembly 340). Alternatively or additionally, a separate device configured to be inserted through endoscope 350 and/or to be positioned alongside endoscope 350, can have one or more lumens configured to deliver the insufflation fluid. System 10 can include one or more occlusive elements and/or devices, such as expandable assembly 130, treatment assembly 140 and/or another expandable device configured to radially expand such as to fully or partially occlude a body lumen, such that insufflation pressure can be achieved and/or maintained over time (e.g. reduce or prevent undesired migration of insufflation fluid). The one or more occlusive elements and/or devices can be positioned proximal to and/or distal to the luminal segment to be insufflated.

Pumping assembly 340 can be configured to remove fluid from a body lumen such as a segment of the gastrointestinal tract. Removed fluids include but are not limited to: delivered ablative fluid; condensate of delivered ablative fluid; insufflation fluids; excess bodily fluids; chyme; digestive fluids; gas; and combinations of these. Fluids can be removed prior to, during and/or after treatment of target tissue TT by treatment element 145. Pumping assembly 340 can be configured to apply a vacuum, such as to remove fluid via at least one treatment element 145, an outflow drain, or other fluid extraction port of system 10. In some embodiments, extracted fluids are recycled, such as for subsequent delivery by at least one treatment element 145 to target tissue TT.

Pumping assembly 340 and/or EDU 330 can be configured to deliver one or more gases (e.g. carbon dioxide, nitrogen, nitrous oxide and/or air) to at least one treatment element 145 or another gas delivering component of system 10. In some embodiments, at least one treatment element 145 comprises a gas jet nozzle configured to deliver gas to target tissue, such as a gas that has been processed to remove moisture or otherwise be dry (e.g. less than the dew point of air, or at a relative humidity less than 20% or less than 10%). In some embodiments, system 10 is configured to deliver gas to cause agitation of an ablative fluid previously delivered within a body lumen. System 10 can be configured to deliver dry or other gas to move ablative fluid in a body lumen. The delivered gas can comprise a cooling gas, such as a gas below 37° C., a gas between 0° C. and 7° C. such as a gas between 2° C. and 7° C., and/or a gas at approximately 4° C. System 10 can deliver cooling gas for a time period of at least 10 seconds, at least 20 seconds or at least 30 seconds. In some embodiments, system 10 delivers cooling gas at a temperature less than 0° C. for a time period less than or equal to 20 seconds, less than or equal to 10 seconds, or less than or equal to 5 seconds. In some embodiments, system 10 is configured to deliver gas at a temperature at or above 42° C., such as to remove moisture or otherwise dry a tissue wall of the gastrointestinal tract. System 10 can be configured to deliver carbon dioxide gas.

Functional element 138 and/or functional element 148 can comprise a sensor. In some embodiments, functional element 138, functional element 148, sensor 353 and/or another sensor of system 10, such as sensor 139 positioned on expandable assembly 130 and/or sensor 149 positioned on treatment assembly 140, can comprise a sensor selected from the group consisting of: temperature sensors such as thermocouples, thermistors, resistance temperature detectors and optical temperature sensors; strain gauges; impedance sensors such as tissue impedance sensors; pressure sensors; blood sensors; optical sensors such as light sensors; sound sensors such as ultrasound sensors; electromagnetic sensors such as electromagnetic field sensors; visual sensors; and combinations of these. The sensors can be configured to provide information to one or more components of system 10, such as to controller 310 and/or EDU 330, such as to monitor the treatment of target tissue TT and/or to treat target tissue TT in a closed loop configuration. Energy delivery from EDU 330 can be initiated, stopped and/or modified based on one or more sensor readings. In one embodiment, an algorithm of controller 310 and/or EDU 330 processes one or more sensor signals to modify an amount of ablative fluid delivered, rate of ablative fluid delivery, temperature of ablative fluid delivered, power of energy delivered, voltage of energy delivered and/or current of energy delivered.

Sensor 149 of treatment assembly 140 can comprise a gravimetric sensor. In these embodiments, sensor 149 can comprise an accelerometer or other sensor configured to provide a signal representing the orientation of treatment assembly 140 and/or treatment element 145 as it relates to the force of earth's gravity. In embodiments in which treatment element 145 delivers ablative fluid to target tissue TT, the signal provided by sensor 149 can provide information for manual and/or automated control of ablative fluid delivery direction. In some embodiments, gravimetric orientation of device 100 is provided to an operator, such as via a screen on controller 310. In some embodiments, the signal from sensor 149 is recorded by controller 310, such as to adjust a spray pattern delivered by treatment assembly 140 and/or treatment element 145. Based on a signal from sensor 149, treatment element 145 and/or shaft 111a can be positioned to deliver ablative fluid in upward and/or side-ways (i.e. horizontal) directions, such as to allow delivered fluid to flow across the walls of a lumen in a downward direction. Controller 310 can be configured to adjust the flow pattern of ablative fluid delivery by adjusting the rotation and/or translation of treatment assembly 140 (e.g. by creating an asymmetric movement). Controller 310 can be configured to adjust the flow pattern of ablative fluid delivery by adjusting which of multiple treatment elements 145 deliver ablative fluid (e.g. by turning on or more one or more electronic fluid valves) or by adjusting a nozzle direction or nozzle flow path geometry of treatment element 145 (e.g. when treatment element 145 comprises a rotatable nozzle and/or a nozzle with an adjustable orifice). In some embodiments, controller 310 utilizes a signal from sensor 149 to manipulate one or more treatment elements 145 to deliver fluid in a relatively upward direction. In some embodiments, system 10 includes a fluid removal element, such as a treatment element 145 configured to remove fluid or an outflow drain, and the fluid removal element is gravimetrically oriented by a signal provided by sensor 149.

Sensors 139 and/or 149 can comprise a chemical detection sensor, such as a chemical detection sensor to confirm proper apposition of expandable assembly 130 and/or treatment assembly 140. In this configuration, a chemical sensor such as a carbon dioxide sensor can be placed distal to expandable assembly 130 and/or treatment assembly 140, and a fluid such as carbon dioxide gas can be introduced proximal to the expandable assembly 130 and/or treatment assembly 140. Detection of the introduced fluid by sensor 139 and/or 149 can indicate inadequate apposition of expandable assembly 130 and/or treatment assembly 140, respectively. Readjustment to achieve sufficient apposition can prevent inadequate treatment of target tissue TT (e.g. inadequate transfer of energy) and/or prevent inadequate measurement, modification, manipulation and/or diagnosis of target tissue TT.

Functional element 138, functional element 148, sensor 139, sensor 149, sensor 353 and/or another sensor of system 10 can be a sensor configured to provide information related to the tissue treatment performed by treatment assembly 140 and/or expandable assembly 130, such as a visual sensor mounted to treatment assembly 140 and/or expandable assembly 130 that is configured to differentiate tissue types that are proximate treatment assembly 140 and/or expandable assembly 130. In some embodiments, system 10 is constructed and arranged to differentiate mucosal and submucosal tissue, such as to adjust one or more treatment parameters (e.g. to stop treatment and/or modify the temperature of treatment) based on the differentiation. Applicable visible sensors include but are not limited to: visible light camera; infrared camera; CT Scanner; MRI; and combinations of these. In some embodiments, energy provided by EDU 330 is based on one or more signals from the visible sensor, such as a sensor providing a signal correlating to tissue color wherein the energy delivered is modified based on a tissue color change. Sensors 149 and 139 can comprise a sensor configured to provide information related to the tissue treatment performed by treatment assembly 140 and/or expandable assembly 130, respectively, such as a temperature sensor configured to monitor the temperature of treatment provided by treatment assembly 140 and/or expandable assembly 130 and/or tissue proximate treatment assembly 140 and/or expandable assembly 130. Sensors 149 and/or 139 can comprise multiple temperature sensors, such as multiple temperature sensors positioned on treatment assembly 140 and/or expandable assembly 130, respectively, with a spacing of at least one sensor per square centimeter. Energy delivered by EDU 330 can be based on signals recorded by the multiple temperature sensors.

Functional element 138 and/or functional element 148 can comprise a transducer. In these and other embodiments, functional element 138, functional element 148, and/or another transducer of system 10 can be a transducer selected from the group consisting of: a heat generating element; a drug delivery element such as an iontophoretic drug delivery element; a magnetic field generator; an ultrasound wave generator such as a piezo crystal; a light producing element such as a visible and/or infrared light emitting diode; and combinations of these.

In some embodiments, EDU 330 and/or another device of component of system 10 is configured to deliver a visualizable material, such as a visualizable material delivered to one or more treatment elements 145. In some embodiments, visualizable material is delivered by treatment element 145 onto and/or beneath the surface of tissue, to assist in the treatment of target tissue TT, such as to assess the status of tissue ablation. In some embodiments, the visualizable material is selected from the group consisting of: radiopaque agent; ultrasonically visible material; magnetically visible material; and combinations of these. An imaging device of system 10, such as imaging device 410 described herebelow, can be used to create an image of the visualizable material during and/or after delivery of the visualizable material.

In some embodiments, EDU 330 or another device of component of system 10 is configured to deliver abrasive particles, such as abrasive particles delivered to one or more treatment elements 145. In some embodiments, visualizable material is also delivered by EDU 330 to assist in the treatment of tissue, such as to improve ablation caused by a mechanical abrasion treatment.

In some embodiments, EDU 330 is configured to deliver at least RF energy, and system 10 includes ground pad 70 configured to be attached to the patient (e.g. on the back of the patient), such that RF energy can be delivered in monopolar delivery mode to one or more electrode-based treatment elements 145 of treatment device 100 or to one or more electrodes of another treatment device of system 10 (e.g. second treatment device 100'). Alternatively or additionally, EDU 330 can be configured to deliver energy in a bipolar RF mode, such as bipolar energy delivered between any two electrode-based treatment elements 145 of treatment device 100 or between any other two electrodes of another treatment device of system 10. Alternatively or additionally, EDU 330 can be configured to deliver energy in a combined monopolar-bipolar mode.

EDU 330 can be configured to deliver RF and/or other forms of energy to one or more treatment elements 145 of treatment assembly 140 and/or a treatment element expandable assembly 130. In some embodiments, EDU 330 delivers energy selected from the group consisting of: RF energy; microwave energy; plasma energy; ultrasound energy; light energy; and combinations of these. Energy can be continuous and/or pulsed, and can be delivered in a closed-loop fashion as described hereabove. Energy delivery parameters such as power, voltage, current and frequency can be held relatively constant or they can be varied by EDU 330. Energy delivery can be varied from a first tissue location (e.g. a first portion of target tissue TT) to a second location (e.g. a second portion of target tissue TT), such as a decrease in energy from a first treated location to a second treated location when the second treated location is thinner than the first treated location. Alternatively or additionally, energy delivery can be varied during a single application of energy to a single tissue location, such as by adjusting one or more energy delivery parameters during a continuous energy delivery. Alternatively or additionally, one or more energy delivery parameters can be varied between a first treatment of target tissue and a second treatment of target tissue, for example a first treatment performed during a first clinical procedure and a second treatment performed during a second clinical procedure, such as when the second treatment is performed at least twenty-four hours after the first treatment, as is described in detail herebelow in reference to FIG. 2.

Pumping assembly 340 and/or EDU 330 typically include one or more fluid pumps, such as one or more peristaltic, displacement and/or other fluid pumps; as well as one or more heat exchangers and/or other fluid heating elements internal and/or external to device 100. Pumping assembly 340 and/or EDU 330 can be configured to rapidly deliver and/or withdraw fluid to and/or from treatment assembly 140 and/or expandable assembly 130 via one or more fluid transport means. Fluid transport means can include a pump configured to deliver fluid at a flow rate of at least 50 ml/min and/or a pump and/or vacuum source configured to remove fluid at a flow rate of at least 50 ml/min. In some embodiments, system 10 is configured to deliver fluid, such as a liquid, at a flow rate of at least 500 ml/min, or at least 750 ml/min A pump and/or vacuum source can be configured to continuously exchange hot fluid and/or to perform a negative pressure priming event to remove fluid from one or more fluid pathways of device 100. Pumping assembly 340, EDU 330, first treatment device 100 and or second treatment device 100' can include one or more valves in the fluid delivery and/or fluid withdrawal pathways or one or more other valves in the fluid pathway within treatment assembly 140 and/or expandable assembly 130. Valves can be configured to control entry of fluid into an area and/or to maintain pressure of fluid within an area. Valves can be used to transition from a heating fluid, such as a fluid of 90° C. maintained in a treatment assembly for approximately 12 seconds, to a cooling fluid, such as a fluid between 4° C. and 10° C. maintained in the assembly element for approximately 30 to 60 seconds. Typical valves include but are not limited to: duck-bill valves; slit valves; electronically activated valves; pressure relief valves; and combinations of these. Pumping assembly 340 and/or EDU 330 can be configured to rapidly inflate and/or deflate treatment assembly 140 and/or expandable assembly 130. Pumping assembly 340 and/or EDU 330 can be configured to purge the fluid pathways of first treatment device 100 and/or second treatment device 100' with a gas such as air, such as to remove cold and/or hot fluid from the devices and/or to remove gas bubbles from the devices.

EDU 330, treatment element 145 and/or other components of system 10 can be configured to treat target tissue TT with a non-desiccating ablation, such as by avoiding tissue temperatures above 100° C., avoiding the creation of steam, or otherwise avoiding deleterious desiccation of tissue. System 10 can be configured to minimize heat production in the outermost 50% of a mucosal layer, such as to ablate the outermost 50% of the mucosal layer via thermal conduction. System 10 can be configured to minimize heat production in the outermost 80% of a mucosal layer, such as to ablate the outermost 80% of the mucosal layer via thermal conduction. System 10 can be configured to maximize the flow of electrical current, such as through the innermost 50% of a mucosal layer, or through the innermost 20% of a mucosal layer. In some embodiments, system 10 can be configured to avoid detachment of tissue particles.

EDU 330, treatment element 145 and/or other components of system 10 can be configured to treat target tissue TT such that the temperature of at least a portion of the target tissue TT rises rapidly, such as at a rate of greater than or equal to 17.5° C. per second. Treatment can be delivered to cause the temperature of at least a portion of the target tissue TT to reach a setpoint temperature between 60° C. and 90° C., such as a setpoint temperature between 65° C. and 85° C. System 10 can be configured to cause the target tissue TT to elevate to a setpoint temperature and maintain that setpoint temperature, such as by maintaining the setpoint temperature for a time period between 2 and 40 seconds. In these embodiments, the setpoint temperature can be between 60° C. and 90° C., such as a setpoint temperature between 65° C. and 85° C. that is maintained for between 5 and 15 seconds. In some embodiments, after a setpoint temperature is achieved and/or maintained, the treatment can be adjusted (e.g. by adjusting energy delivery from EDU 330) such that tissue temperature decreases over time, such as to match a tissue response of the target tissue TT.

Controller 310 can include a graphical user interface configured to allow one or more operators of system 10 to perform one or more functions such as entering of one or more system input parameters and visualizing and/or recording of one or more system output parameters. Controller 310 can include one or more user input components (e.g. touch screens, keyboards, joysticks, electronic mice and the like), and one or more user output components (e.g. video displays; liquid crystal displays; alphanumeric displays; audio devices such as speakers; lights such as light emitting diodes; tactile alerts such as assemblies including a vibrating mechanism; and the like). Examples of system input parameters include but are not limited to: temperature of ablative fluid to be delivered such as temperature of fluid to be delivered to a nozzle or to an expandable reservoir such as a balloon; type of ablative fluid to be delivered; rate of ablative fluid to be delivered; volume of ablative fluid to be delivered; type of energy to be delivered such as RF energy, thermal energy and/or mechanical energy; quantity of energy to be delivered such as a cumulative number of joules of energy to be delivered and/or peak amount of energy to be delivered; types and levels of combinations of energies to be delivered; energy delivery duration; pulse width modulation percentage of energy delivered; temperature of a cooling fluid to be delivered; temperature of a priming fluid to be delivered; flow rate of a fluid to be delivered; volume of a fluid to be delivered; number of reciprocating motions for an energy delivery element to transverse; temperature for a treatment assembly such as target temperature and/or maximum temperature; insufflation pressure; insufflation duration; and combinations of these. System input parameters can include information based on patient anatomy and/or conditions such as pre-procedural and/or peri-procedural parameters selected from the group consisting of: mucosal density and/or thickness; mucosal "lift" off of submucosa after a submucosal injection; longitudinal location of target tissue within the GI tract; and combinations of these. Examples of system output parameters include but are not limited to: temperature information such as tissue and/or treatment assembly temperature information; pressure information such as balloon pressure information and/or insufflation pressure information; force information such as level of force applied to tissue information; patient information such as patient physiologic information recorded by one or more sensors; and combinations of these.

Controller 310 and/or one or more other components of system 10 can include an electronics module, such as an electronics module including a processor, memory, software, and the like. Controller 310 is typically configured to allow an operator to initiate, modify and cease treatment of target tissue TT by the various components of system 10, such as by controlling EDU 330 and/or pumping assembly 340. Controller 310 can be configured to modify one or more tissue treatment parameters, such as a parameter selected from the group consisting of: temperature of an ablative fluid to be delivered directly to tissue or to an expandable reservoir such as a balloon; type of ablative fluid to be delivered; rate of ablative fluid to be delivered; volume of ablative fluid to be delivered; pulse width modulation on-time and/or off-time; a time division multiplexing parameter; and combinations of these. Controller 310 can be configured for manual control, so that the operator first initiates the tissue treatment, then allows the treatment element 145 and/or another associated treatment element to treat the target tissue TT for some time period, after which the operator terminates the treatment.

Controller 310 and EDU 330 can be configured to treat target tissue TT in constant, varied, continuous and discontinuous energy delivery or other treatment delivery profiles. Pulse width modulation and/or time division multiplexing (TDM) can be incorporated to achieve precision of an ablative treatment, such as to ensure ablation of target tissue TT while leaving non-target tissue intact.

In some embodiments, where system 10 is further configured to perform hot fluid ablation, controller 310 can be configured to adjust the temperature, flow rate and/or pressure of fluid delivered to an expandable reservoir, such as when treatment assembly 140 and/or expandable assembly 130 comprise a balloon. Controller 310 can be configured to initiate insufflation and/or to adjust insufflation pressure. Controller 310 can be configured to deliver energy or otherwise treat target tissue in a closed-loop fashion, such as by modifying one or more tissue treatment parameters based on signals from one or more sensors of system 10, such as those described hereabove. Controller 310 can be programmable such as to allow an operator to store predetermined system settings for future use.

Controller 310 can comprise an impedance monitoring assembly, such as an impedance monitoring assembly that receives impedance information from one or both of sensor 139 of expandable assembly 130 and/or sensor 149 of treatment assembly 140. EDU 330 can deliver RF energy to one or more electrode-based treatment elements of system 10 based on the impedance determined by the impedance monitoring assembly.

Numerous embodiments of the systems, methods and devices for treating target tissue TT described hereabove include controlling and/or monitoring the change in target tissue temperature to cause its ablation, such as a temperature increase above 43° C., typically above 60° C., 70° C. or 80° C., to ablate at least a portion of the target tissue TT. One or more cooling fluids can be delivered to limit or otherwise control ablation, such as to prevent damage to non-target tissue, such as the duodenal adventitia. Pumping assembly 340 can be configured to deliver a fluid to tissue and/or a component and/or assembly of system 10, such as to warm and/or cool the tissue, component and/or assembly. Pumping assembly 340 can be configured to deliver a cooling fluid to a luminal wall such as the duodenal wall, such as prior to a delivery of energy, during a delivery of energy and/or after a delivery of energy. In some embodiments, a chilled fluid is used to cool tissue prior to, during and/or after a high temperature ablation of tissue. System 10 can be configured to deliver a fluid at a temperature below 37° C. or below 20° C. The chilled fluid can be delivered at a temperature between 0° C. and 7° C., and in some embodiments, the chilled fluid is delivered at a temperature less than 0° C. System 10 to can be configured to deliver chilled fluid at multiple temperatures to target tissue TT and/or other tissue. System 10 can be configured to deliver a first chilled fluid at a first temperature for a first time period, followed by a second chilled fluid delivered at a second temperature for a second time period. The first and second chilled fluids can be similar or dissimilar fluids, such as similar or dissimilar liquids and/or gases. In some embodiments, the first chilled fluid is colder than the second chilled fluid, such as a first chilled fluid delivered at approximately 4° C. for a time period of approximately 5 seconds, followed by fluid delivered at a higher temperature (e.g. a temperature between 10° C. and 37° C.) for a time period of at least 5 seconds. The chilled fluid can be delivered between treatment of a first portion of target tissue and a second portion of target tissue (e.g. to the same or different tissue), such as to remove residual heat remaining after the first treatment. The cooling fluid can be delivered through functional element 138 of expandable assembly 130 and/or functional element 148 of treatment assembly 140, such as when functional elements 138 and/or 148 comprise a fluid delivery element such as a nozzle, an exit hole, a slit, or a permeable membrane. The cooling fluid can be supplied to a location within expandable assembly 130 and/or treatment assembly 140, such as when expandable assembly 130 and/or treatment assembly 140 comprises a balloon or other expandable reservoir configured to contact tissue. Alternatively or additionally, pumping assembly 340 can be fluidly attached to another component of treatment device 100 and/or system 10, the attached component not shown but configured to deliver fluid to tissue and/or a component of system 10 such as to add and/or absorb heat. Pumping assembly 340 can comprise a cryogenic source used to deliver fluids at low temperatures, such as temperatures below 0° C. Typical fluids delivered include but are not limited to: liquids such as water and/or saline; gases such as carbon dioxide, nitrogen, nitrous oxide and/or air; and combinations of these.

Pumping assembly 340 can include a desiccant and/or drying assembly configured to dehydrate or otherwise remove moisture from one or more delivered gases prior to their delivery. In some embodiments, fluid provided to one or more treatment elements 145 has its temperature modified by a component in a distal portion of device 100, such as a heating or cooling element integral or proximal to treatment element 145 (e.g. a pettier cooling element, an expanded gas cooling assembly, or a heating coil integral to treatment element 145). Alternatively or additionally, system 10 can include a component configured to directly contact tissue in order to cool or warm tissue. In some embodiments, radially expandable element 131, functional element 138 and/or functional element 148 can be configured to contact tissue and remove and/or add heat from the contacted tissue.

System 10 can include a motion control mechanism, such as motion transfer assembly 320. Motion transfer assembly 320 can be configured to rotate, translate and/or otherwise move a component of system 10, such as to move one or more of treatment assembly 140, treatment element 145 and/or expandable assembly 130. In some embodiments, motion transfer assembly 320 is configured to rotate and/or axially translate shafts 111a and/or 111b such that treatment assembly 140 and/or expandable assembly 130, respectively, are rotated and/or translated. Motion transfer assembly 320 can be configured to rotate treatment assembly 140 and/or expandable assembly 130 independently or in unison. Motion transfer assembly 320 can be configured to translate treatment assembly 140 as treatment is applied to a portion of target tissue TT. In some embodiments, contiguous tissue portions are treated by device 100 continuously as motion transfer assembly 320 causes treatment assembly 140 to translate at a rate of at least 10 cm per minute, or at a rate of at least 20 cm per minute. In some embodiments, treatment assembly 140 is manually translated, such as at a rate of at least 10 cm per minute, or at least 20 cm per minute. Motion transfer assembly 320 can be configured to translate treatment assembly 140 between a first tissue treatment and a second tissue treatment. Motion transfer assembly 320 can include one or more rotational and/or linear drive assemblies, such as those including rotational motors, magnetic drives, lead screw and/or other linear actuators, and the like which are operably connected to shaft 111a and/or 111b. Shafts 111a and/or 111b are constructed with sufficient column strength and/or torque transfer properties to sufficiently rotate and/or translate treatment assembly 140 and/or expandable assembly 130, respectively. Motion transfer assembly 320 can be in communication with controller 310, such as to activate, adjust and/or otherwise control motion transfer assembly 320 and thus the motion of treatment assembly 140 and/or expandable assembly 130. Motion transfer assembly 320 can be manually driven and/or automatically (e.g. motor) driven. Alternatively or additionally, motion transfer assembly 320 can be used to advance and/or retract treatment assembly 140 and/or expandable assembly 130 from a first position to treat a first portion of target tissue, to a second position to treat a second portion of target tissue. In this embodiment, repositioning of treatment assembly 140 and/or expandable assembly 130 can be configured to provide overlapping treatment, such as the overlapping treatment described in reference to FIG. 3 herebelow.

System 10 can include one or more additional treatment devices, such as second treatment device 100'. Second treatment device 100' and/or other treatment devices of the present inventive concepts can be configured to treat target tissue TT in the same clinical procedure, or in a clinical procedure performed at least twenty-four hours after the first clinical procedure. Second treatment device 100' can be of similar or dissimilar construction to treatment device 100. In some embodiments, second treatment device 100' comprises an expandable assembly with a different diameter than expandable assembly 130 of device 100. In some embodiments, second treatment device 100' comprises a treatment element with a different construction and arrangement than treatment element 145 of treatment device 100. In some embodiments, second treatment device 100' comprises a device selected from the group consisting of: hot fluid filled balloon device; RF energy delivery device; vapor ablation device; cryoablation device; laser ablation device; ultrasound ablation device; mechanical abrasion device; and combinations of these. Second treatment device 100' can comprise at least one ablation element selected from the group consisting of: an RF energy delivery element such as one or more electrodes, each comprising one or more elongate conductors; an ultrasonic transducer such as one or more piezo crystals configured to ablate tissue; a laser energy delivery element such as one or more optical fibers and/or laser diodes; a heat delivery element such as a hot fluid filled balloon; a rotating ablation element; a circumferential array of ablation elements; and combinations of these.

System 10 can further include one or more imaging devices, such as imaging device 410. Imaging device 410 can be configured to be inserted into the patient and can comprise a visual light camera; an ultrasound imager; an optical coherence domain reflectometry (OCDR) imager; and/or an optical coherence tomography (OCT) imager, such as when integral to, attached to, contained within and/or proximate to shaft 111a and/or 111b. Imaging device 410 can be inserted through a separate working channel of endoscope 350, lumen not shown. In one embodiment, imaging device 410 is an ultrasound transducer connected to a shaft, not shown but surrounded by shaft 111a and typically rotated and/or translated to create a multi-dimensional image of the area surrounding imaging device 410. Alternatively or additionally, imaging device 410 can be external to the patient, such as an imaging device selected from the group consisting of: an X-ray; a fluoroscope; an ultrasound image; an MRI; a PET Scanner; a near-infrared imaging camera; a fluorescence imaging camera; and combinations of these. Image and other information provided by imaging device 410 can be provided to an operator of system 10 and/or used by a component of system 10, such as controller 310, to automatically or semi-automatically adjust one or more system parameters such as one or more energy delivery parameters.

System 10 can further include protective element 191, configured to be positioned proximate tissue to prevent damage to certain tissue during tissue ablative fluid delivery, other energy delivery and/or other tissue treatment event. Protective element 191 can comprise an element selected from the group consisting of: a deployable and/or recoverable cap and/or covering; an advanceable and/or retractable protective sheath; and combinations of these. Protective element 191 can be delivered with endoscope 350 and/or another elongate device such that protective element 191 can be placed over or otherwise positioned to protect non-target tissue, such as tissue selected from the group consisting of: ampulla of Vater, bile duct, pancreas, pylorus, muscularis externae, serosa; and combinations of these. In some embodiments, protective element 191 is placed prior to treatment of at least a portion of target tissue TT, and removed in the same clinical procedure. In other embodiments, protective element 191 is implanted in a first clinical procedure, and removed in a second clinical procedure, such as a second clinical procedure as described in reference to FIG. 2 herebelow. System 10 can be configured to identify non-target tissue, such as via a camera used to identify the ampulla of Vater.

System 10 can be configured to prevent excessive distension of the duodenum such as distension that could cause tearing of the serosa. In some embodiments, system 10 is configured such that all tissue contacting components and/or fluids delivered by system 10 maintain forces applied on a gastrointestinal wall below 1.0 psi, such as less than 0.5 psi, or less than 0.3 psi. System 10 can be configured to avoid or otherwise minimize damage to the muscularis layer of the gastrointestinal tract, such as by controlling pressure of target tissue treatment (e.g. via controlling expansion force of treatment assembly 140 and or expandable assembly 130) and/or by otherwise minimizing trauma imparted on any tissue by one or more components of system 10.

System 10 can further include one or more pharmaceutical and/or other agents 420, such as an agent configured for systemic and/or local delivery to a patient. These agents can be delivered pre-procedurally, peri-procedurally and/or post-procedurally. The agents can be configured to improve healing, such as agents selected from the group consisting of: antibiotics, steroids, mucosal cytoprotective agents such as sucralfate, proton pump inhibitors and/or other acid blocking drugs; and combinations of these. Alternative or in addition to these agents, pre-procedural and/or post-procedural diets can be employed. Pre-procedural diets can include food intake that is low in carbohydrates and/or low in calories. Post-procedural diets can include food intake that comprise a total liquid diet and/or a diet that is low in calories and/or low in carbohydrates.

In some embodiments, system 10 does not include a chronically implanted component and/or device, only body inserted devices that are removed at the end of the clinical procedure or shortly thereafter, such as devices removed within 8 hours of insertion, within 24 hours of insertion and/or within one week of insertion. In an alternative embodiment, implant 192 can be included. Implant 192 can comprise at least one of: a stent; a sleeve; and/or a drug delivery device such as a coated stent, a coated sleeve and/or an implanted pump Implant 192 can be inserted into the patient and remain implanted for a period of at least one month, at least 6 months or at least 1 year. In some embodiments, a first clinical procedure is performed treating target tissue, and a subsequent second clinical procedure is performed, as is described in reference to FIG. 2 herebelow. In these two clinical procedure embodiments, a device can be implanted in the first clinical procedure, and removed in the second clinical procedure.

Any of the components of system 10 can include a coating, such as a lubricious coating. In some embodiments, treatment elements 145 and/or radially expandable elements such as balloons include a lubricious or other material property modifying coating. In some embodiments, a radially expandable treatment assembly 140 and/or assembly 130 comprise a hydrophilic coating, for example configured to disperse or otherwise move an ablative fluid.

Each of the components and/or devices of system 10 can be removably attached to another component, particularly treatment device 100, controller 310, EDU 330, motion transfer assembly 320, pumping assembly 340, ground pad 70, endoscope 350 and/or second treatment device 100'. Typical attachment means include but are not limited to mechanical or electromechanical connectors providing an electrical, optical and/or fluidic connection between the attached components.

Figure 2:
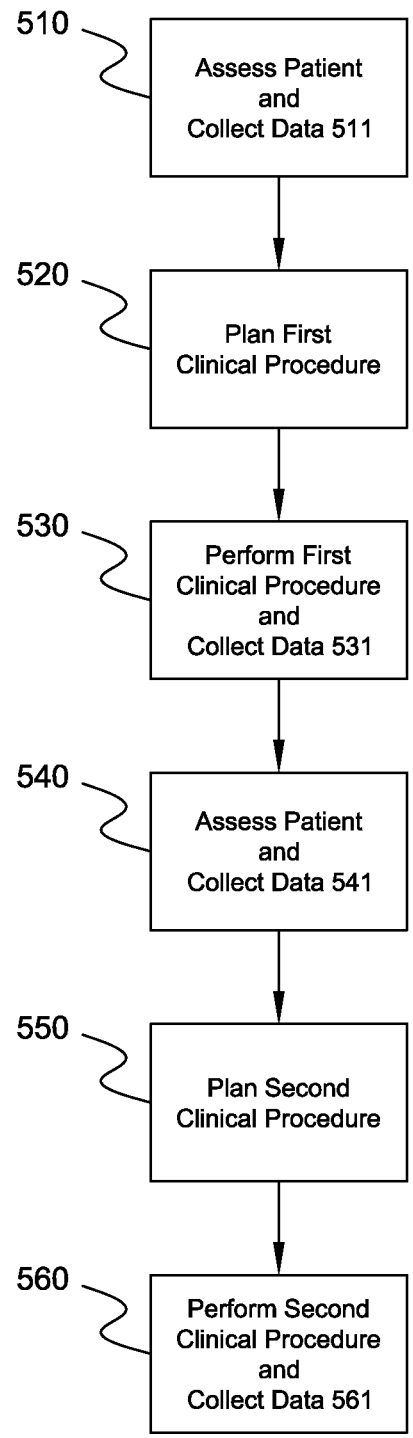
FIG. 2 is a flow chart of a method for treating a patient comprising performing a first tissue treatment in a first clinical procedure and performing a second tissue treatment in a second clinical procedure, consistent with the present inventive concepts.

Referring now to FIG. 2, a flow chart of a method for treating a patient comprising performing a first tissue treatment in a first clinical procedure and a second tissue treatment in a second clinical procedure is illustrated, consistent with the present inventive concepts. In STEP 510, a patient assessment is performed. In some embodiments, data 511 can be collected, such as data collected in a diagnostic procedure performed on the patient. The assessment can include an assessment of a patient disease or disorder, such as a disease or disorder selected from the group consisting of: diabetes; obesity or otherwise being overweight; hypercholesterolemia; exercise intolerance; psoriasis; and combinations of these.

Based on the assessment performed in STEP 510, a clinical procedure can be planned in STEP 520. The planning can include determining the value of one or more procedural parameters for a first clinical procedure to be performed on the patient, as well as one or more additional clinical procedures to be performed on the patient. Procedural parameters can include but are not limited to: location of tissue to be treated; device configuration to be used to treat tissue such as configuration of one or more energy delivery parameters; number of clinical procedures to be performed; time duration between a first clinical procedure and a second clinical procedure; and combinations of these.

In STEP 530, a first clinical procedure is performed based on the planning performed in STEP 520. The clinical procedure can be performed using a system constructed and arranged to treat target tissue, such as system 10 of FIG. 1. Target tissue can be treated using one or more tissue treatment devices such as first treatment device 100 and/or second treatment device 100' of FIG. 1. Target tissue can be treated in multiple steps, such as multiple energy delivery steps as is described in reference to FIG. 3 herebelow.

During the performance of the first clinical procedure in STEP 530, data 531 can be collected, such as data collected during one or more diagnostic procedures performed during the first clinical procedure.

After a time period has elapsed, STEP 540 can be performed. STEP 540 can comprise performing a second patient assessment, similar or dissimilar to the patient assessment performed in step 510. Alternatively or additionally, STEP 540 can comprise collecting data 541, such as data collected in one or more diagnostic procedures performed in STEP 540.

STEP 550 comprises the planning of at least a second clinical procedure. Step 550 can be performed directly after the performance of the first clinical procedure of STEP 530, or after the optional performance of step 540 where a patient assessment is performed and/or data 541 is collected. STEP 550 can include similar or dissimilar planning steps to the planning steps performed in STEP 520.

In STEP 560, a second clinical procedure is performed, such as a treatment of tissue performed at least twenty-four hours after the tissue treatment performed in the first clinical procedure of STEP 530. In some embodiments, the second clinical procedure is performed at least 1 week, at least 1 month, at least 6 weeks, at least 3 months, at least 6 months or at least one year after the performance of the first clinical procedure. In some embodiments, the second clinical procedure is performed at least 3 years or at least 5 years after the performance of the first clinical procedure. The time duration between the first clinical procedure and the second clinical procedure can be pre-determined, such as a determination made prior to the performance of the clinical procedure in STEP 530, during the performance of the first clinical procedure, or after the performance of the first clinical procedure. The time duration between the first clinical procedure and the second clinical procedure can be based on patient or procedural data, such as data 511 collected in STEP 510, data 531 collected in STEP 530 and/or data 541 collected in STEP 540.

In the first clinical procedure performed in STEP 530, the target tissue treated can include at least duodenal tissue, such as at least a portion of the mucosal layer of the duodenum. In some embodiments, the first clinical procedure can also treat jejunal mucosal tissue; ileal mucosal tissue and/or gastric mucosal tissue. The target tissue treated can include a full or partial circumferential portion of a segment of GI tissue, such as a full or partial circumferential portion of a segment of duodenal tissue. Partial circumferential portions of treated tissue can comprise 45° to 350° partial segments, as has been described hereabove.

The target tissue treated in STEP 530 and/or STEP 560 can comprise an area (e.g. a cross-sectional area) and/or a volume that is limited to prevent the occurrence of an adverse event such as a hypoglycemic event or damage to deeper non-target tissue structures. The target tissue treated can comprise an area and/or a volume that is limited to allow reduced duration of healing, such as a target tissue area and/or volume comprising an axial segment of duodenum with a length of less than 6 inches, or less than 4 inches.

In some embodiments, the clinical procedures performed in STEP 530 and/or STEP 560 can include the implanting of a device, such as a device implanted in the GI tract such as implant 192 of FIG. 1. In a particular embodiment, a device is implanted in the patient in the first clinical procedure of STEP 530 and removed in the second clinical procedure of STEP 560. In some embodiments, a first device is implanted in the first clinical procedure, and a second device is implanted in the second clinical procedure.

Treatment of target tissue in the clinical procedures performed in STEP 530 and/or STEP 560 can include tissue treatment with an ablative or non-ablative tissue treating device. In some embodiments, target tissue treated in the first and/or second clinical procedures includes treatment of target tissue with an ablative device such as an ablative fluid balloon or RF energy delivery device. In some embodiments, target tissue treated in the first and/or second clinical procedures includes treatment of tissue with a device constructed and arranged to perform a treatment selected from the group consisting of: mechanical removal of mucosal tissue; sclerosant injection into the submucosa; radioactive seed deposition; chemical spray such as an acid spray; pharmacologic administration such as drug delivery via an agent-eluting balloon; and combinations of these. Various forms of tissue treatment systems, devices and methods can be used in the first and/or second clinical procedures, such as those described hereabove in reference to FIG. 1.

In some embodiments, the first clinical procedure of STEP 530 provides a therapeutic benefit to the patient that decreases over time, and the second clinical procedure of STEP 560 is performed to provide time-extended therapeutic benefit to the patient, such as near to, at or above the therapeutic benefit achieved as a result of the first clinical procedure. Additional clinical procedures (e.g. a third, fourth, etc) can be performed, using similar or dissimilar systems, devices and methods to either the first clinical procedures or the second clinical procedure. Three or more clinical procedures can be performed with similar or dissimilar time periods between treatments. In some embodiments, repeated procedures are performed at substantially similar intervals, such as at intervals between 6 months and 5 years.

In some embodiments, a desired therapeutic benefit is achieved through the performance of multiple clinical procedures, such as a therapeutic benefit that results from the combined treatments of first clinical procedure of STEP 530 and the second clinical procedure of STEP 560. In some embodiments, a first level of therapeutic benefit is achieved after the performance of the first clinical procedure of STEP 530, and an elevated therapeutic benefit is achieved after the performance of the second clinical procedure of STEP 560. For example, the first clinical procedure can achieve a therapeutic benefit including a first level of improvement of the disease or disorder, and the second clinical procedure can achieve a second level of improvement of the disease or disorder, greater than the first level of improvement. Levels of improvement can include but are not limited to: the length of time in which one or more disease or disorder improvements are maintained; reduction in magnitude of one or more disease or disorder-caused adverse conditions or symptoms; improvement in diagnostic results collected in one or more diagnostic procedures such as those described below in reference to this figure; and combinations of these. In some embodiments, the performance of the second clinical procedure can be based on the first level of therapeutic benefit.

In some embodiments, the first clinical procedure of STEP 530 comprises treating a first portion of tissue comprising less than 100% of the duodenal mucosa, such as less than 67% of the duodenal mucosa or less than 50% of the duodenal mucosa. In these embodiments, the second clinical procedure of STEP 560 can treat a second portion of tissue comprising substantially more, such as substantially the remaining portion of the duodenal mucosa (i.e. the portion of the duodenal mucosa not-treated in the first clinical procedure). In some embodiments, the second clinical procedure of STEP 560 can treat a deeper volume of tissue (e.g. via deeper penetration of energy into the duodenal wall) than the volume of tissue treated in the first clinical procedure of STEP 530. In some embodiments, the second clinical procedure of STEP 560 can treat a larger cross sectional area of tissue (e.g. by extending the treatment further circumferentially or axially within the intestine) that the cross sectional area of tissue treated in the first clinical procedure of STEP 530. The second portion of tissue treated in the second clinical procedure can further include one or more subportions of the first tissue portion (i.e. tissue treated earlier) as well as additional (e.g. non-duodenal) tissue.

The first clinical procedure of STEP 530 and/or the second clinical procedure of STEP 560 can include one or more tissue expansion procedures, such as a tissue expansion procedure performed by tissue expansion device 200 of FIG. 1. In some embodiments, the first and/or second clinical procedures include a tissue expansion device or method as is described in applicant's co-pending U.S. Provisional Application Ser. No. 61/635,810, entitled "Tissue Expansion Devices, Systems and Methods", filed Apr. 19, 2012, the contents of which are incorporated herein by reference in its entirety. Tissue expansion can be performed in multiple steps and/or with multiple injections of tissue expanding fluids.

The first clinical procedure of STEP 530 and/or the second clinical procedure of STEP 560 can include treatment of target tissue performed in multiple steps, such as treatments including multiple sequential energy deliveries; multiple deliveries of ablative fluid directly to tissue or to a reservoir such as a balloon; multiple applications of a mechanically abrasive element to tissue; and combinations of these.

Figure 4:
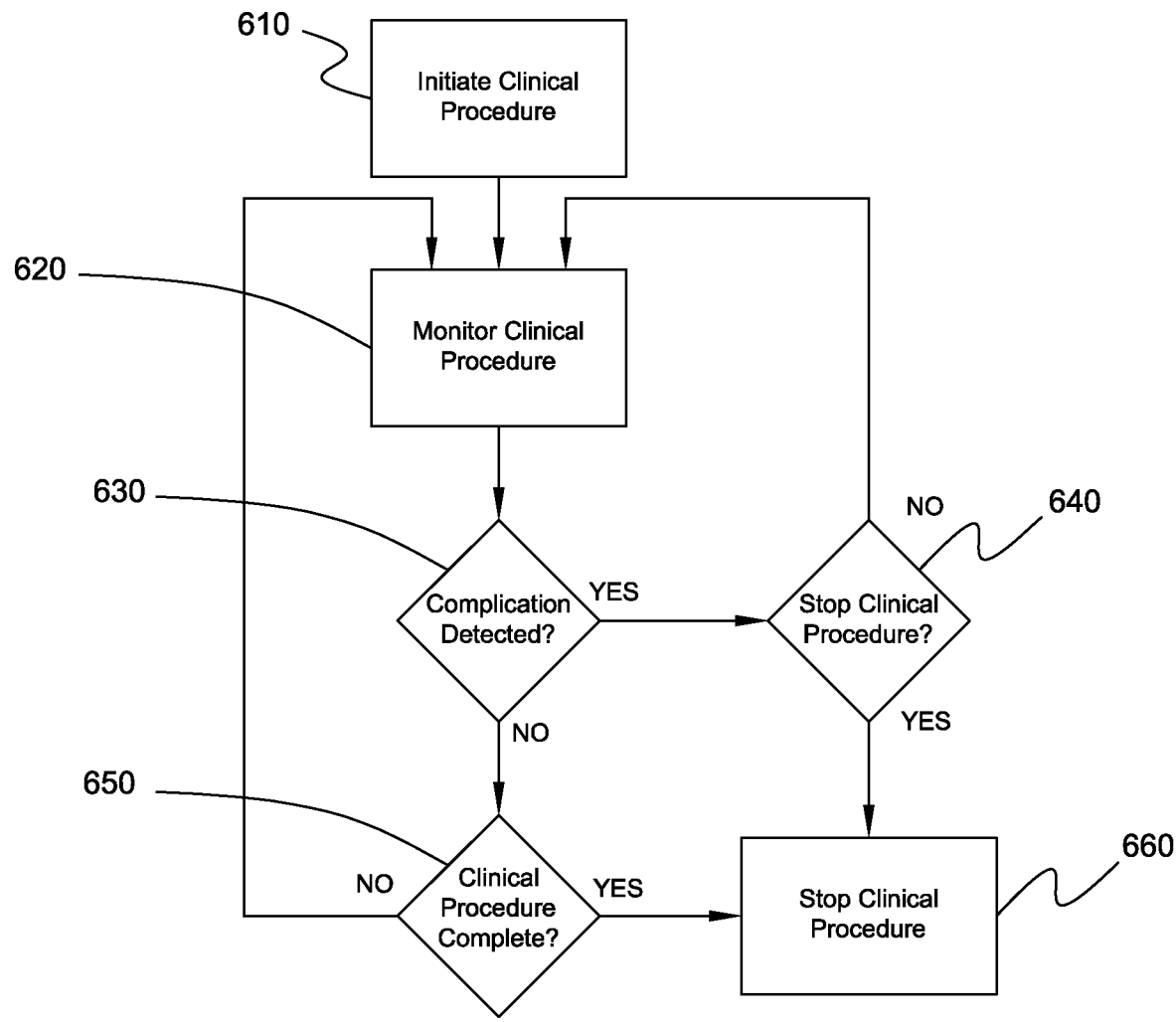
FIG. 4 is a flow chart of a method for treating a patient comprising monitoring a tissue treatment procedure, consistent with the present inventive concepts.

The first clinical procedure of STEP 530 and/or the second clinical procedure of STEP 560 can be stopped prior to a planned sub-procedural step, such as is described in reference to FIG. 4 herebelow. In these embodiments, a subsequent clinical procedure can be scheduled to achieve a desired therapeutic benefit (e.g. schedule of the second clinical procedure of STEP 560 after an incomplete first clinical procedure results in STEP 530).

The first clinical procedure of STEP 530 can comprise similar or dissimilar systems, devices and/or methods to the systems, devices and methods of the second clinical procedure of STEP 560. Examples of dissimilar systems, devices and methods are described immediately herebelow.

As described above, one or more diagnostic procedures can be performed in the method of the present inventive concepts, such as to produce diagnostic results such as data 511, data 531, data 541 and/or data 561 collected in STEP 510, STEP 530, STEP 540 and/or STEP 560, respectively. Diagnostic results can be collected in any step, such as prior to performing the first clinical procedure in STEP 530, prior to performing the second clinical procedure in STEP 560, and any time thereafter (e.g. between a third and fourth clinical procedure). Diagnostic results can be collected using one or more diagnostic tools. In some embodiments, treatment device 100 and/or another component of system 10 of FIG. 1 is configured to collect diagnostic results. In some embodiments, a separate diagnostic tool is provided.

Data 511, data 531, data 541, data 561 and/or any other collected diagnostic results, as well as data representing mathematically or otherwise processed diagnostic results (collectively "diagnostic results"), can be used to determine one or more system, device and/or method configuration parameters. The diagnostic results can represent a fixed value for one or more physiologic or other patient or procedural parameters (a number of examples of which are described in detail herebelow). Alternatively or additionally, the diagnostic results can represent the rate of change or other measure of one or more such parameters.

Mathematical or other processing of one or more diagnostic results can be performed, such as a manual processing or an automated processing. In some embodiments an automated or semi-automated processing is performed by controller 310 of system 10 of FIG. 1. Applicable processing can include data processing functions selected from the group consisting of: averaging; determining minimum and/or maximum values; integrating; sampling; applying a transfer function; and combinations of these. System 10 can include one or more algorithms or otherwise be configured to perform the analysis, such as an analysis that mathematically processes one or more diagnostic results to produce additional diagnostic results. System 10 can include one or more algorithms or otherwise be configured to perform an analysis that compares diagnostic results to one or more threshold values, or threshold ranges (hereinafter, collectively a "threshold comparison"). Results of one or more analyses can be used to manually, semi-automatically or automatically modify and/or configure a system, device and/or method of the present inventive concepts, such as a modification made between the first clinical procedure and the second clinical procedure.

In some embodiments, the second clinical procedure is modified from the first clinical procedure based on data collected during and/or after the performance of the first clinical procedure, such as data 531 and/or data 541 which each can include data collected during the performance of one or more diagnostic procedures. In some embodiments, the second clinical procedure is modified from the first clinical procedure based on an analysis of diagnostic results, such as data 511, data 531, data 541 and/or data 561, or diagnostic results comprising results of processing one or more of these data.

In some embodiments, the second clinical procedure comprises a different type of treatment device, such as when the first clinical procedure comprises an ablative or non-ablative treatment device, and wherein the second clinical procedure comprises the opposite treatment device. In some embodiments, the second clinical procedure treatment device is selected based on an analysis of diagnostic results, such as data 511, data 531, data 541 and/or data 561, or diagnostic results comprising results of processing one or more of these data.

In some embodiments, the second clinical procedure delivers energy in a different manner than energy delivered in the first clinical procedure, such as a difference in energy type, level and/or amount. Numerous energy settings and/or configurations can be modified, such as those described in reference to system 10 of FIG. 1. In some embodiments, one or more second clinical procedure energy delivery parameters are selected based on an analysis of diagnostic results, such as data 511, data 531, data 541 and/or data 561, or diagnostic results comprising results of processing one or more of these data.

The first clinical and second clinical procedures can comprise different areas and/or volumes of target tissue treated, such as different axial or circumferential segments of GI tissue. In some embodiments, the second clinical procedure comprises a larger area and/or volume of target tissue treated, such as when the first clinical procedure treats a volume of tissue less than 50% of the duodenal mucosa and the second clinical procedure treats more than 50% of the duodenal mucosa. In some embodiments, the second clinical procedure treatment area and/or volume is selected based on an analysis of diagnostic results, such as data 511, data 531, data 541 and/or data 561, or diagnostic results comprising results of processing one or more of these data.

The first and second clinical procedure can comprise treating target tissue in similar and/or dissimilar locations, such as two independent portions of tissue or tissue portions that have similar (e.g. overlapping) and dissimilar locations. In some embodiments, the second clinical procedure treats tissue that was not treated in the first clinical procedure, such as tissue that was identified as being untreated in a patient assessment performed after the first procedure is completed, such as the patient assessment performed in STEP 540. The tissue treated in the second clinical procedure can include untreated tissue that borders tissue treated in the first clinical procedure. Tissue treated in the first clinical procedure can comprise a limited amount of tissue, such as tissue limited to the duodenum, and the tissue treated in the second clinical procedure can include previously untreated tissue selected from the group consisting of: jejunal mucosa; ileal mucosa; gastric mucosa; and combinations of these. In some embodiments, the second clinical procedure tissue treatment location device is selected based on an analysis of diagnostic results, such as data 511, data 531, data 541 and/or data 561, or diagnostic results comprising results of processing one or more of these data.

Either or both the first and second clinical procedures can each include a tissue expansion procedure, such as a second tissue expansion procedure performed in the second clinical procedure that is different than a first tissue expansion procedure performed in the first clinical procedure. In some embodiments, a different volume of tissue expansion fluid is used in each clinical procedure, such when more tissue expansion fluid is used in the second clinical procedure (e.g. to apply sufficient pressure to expand healed, previously treated tissue) or when less tissue expansion fluid is used in the second clinical procedure (e.g. to cause tissue expansion in the second clinical procedure to be less than tissue expansion in the first clinical procedure). In some embodiments, a different pattern of tissue expanding fluid injections is performed in the second clinical procedure than were performed in the first clinical procedure, such as a denser pattern (e.g. a denser pattern used to increase expansion of tissue) or a less dense pattern (e.g. a less dense pattern correlating to a maximum amount of fluid that can be maintained in the expanded tissue region). In some embodiments, a different amount of cross sectional area of tissue is expanded in the second clinical procedure as compared to the first clinical procedure, such as an increased area in the second clinical procedure (e.g. to expand tissue to be treated in the second clinical procedure that wasn't treated in the first clinical procedure) or a decreased area in the second clinical procedure (e.g. to expand less tissue in the second clinical procedure than was expanded in the first clinical procedure). In some embodiments, tissue expanded in the second clinical procedure comprises tissue at a location different than tissue expanded in the first clinical procedure, such as tissue that is more distal and/or more proximal (e.g. more distal or more proximal in the GI tract) to tissue expanded in the first clinical procedure, or tissue comprising a partial circumferential segment that was not expanded and/or treated in the first clinical procedure. In some embodiments, tissue expansion fluid used to expand tissue in the second clinical procedure differs from the tissue expansion fluid used to expand tissue in the first clinical procedure. In some embodiments, a tissue expansion device used in the second clinical procedure differs from a tissue expansion device used in the first clinical procedure. In some embodiments, the first and/or second clinical procedure tissue expansion configuration is selected based on an analysis of diagnostic results, such as data 511, data 531, data 541 and/or data 561, or diagnostic results comprising results of processing one or more of these data.

In some embodiments, the diagnostic results are used to determine one or more parameters regarding a tissue portion to be treated in the first or second clinical procedure. Examples of such tissue portion parameters include but are not limited to: anatomical location or locations; tissue volume amount; depth of tissue to be treated; and combinations of these. In some embodiments, the area or volume of the tissue treated in the second clinical procedure is based on comparison of one or more diagnostic results to a threshold, such as when the area or volume treated in the second clinical procedure is larger than the area or volume treated in the first clinical procedure when the diagnostic results are below a threshold, and smaller when the diagnostic results are above the threshold. In some embodiments, less than 50% of the duodenal mucosa is treated in the first clinical procedure, and if a diagnostic result is less than a threshold, at least 90% of the duodenal mucosa is treated in the second clinical procedure. In some embodiments, the one or more tissue portion parameters of the second clinical procedure is selected based on an analysis of diagnostic results, such as data 511, data 531, data 541 and/or data 561, or diagnostic results comprising results of processing one or more of these data.

Diagnostic results can be used to determine the elapsed time between the first clinical procedure and the second clinical procedure. In some embodiments, the elapsed time between the first clinical procedure and the second clinical procedure is selected based on an analysis of diagnostic results, such as data 511, data 531, data 541 and/or data 561, or diagnostic results comprising results of processing one or more of these data.

Diagnostic results can include numerous forms of physiologic or other patient parameters. In some embodiments, the diagnostic results comprise results collected in performing a clinical test, such as a test comprising an assessment of one or more of: body weight; body mass index (BMI); blood pressure; and combinations of these. In some embodiments, diagnostic results include data collected in the performance of an efficacy serum test, such as an efficacy serum test assessing a parameter selected from the group consisting of: hemoglobin A1c (HgbA1c); post-meal or post-glucose tolerance test glucose; insulin; C-peptide; glucagon; GIP; GLP-1; LDL; HDL; triglycerides; and combinations of these. In some embodiments, diagnostic results include data collected in the performance of a fasting serum test, such as a fasting serum test assessing a parameter selected from the group consisting of: glucose; insulin; HOMA-IR; C-peptide; glucagon; GIP; GLP-1; LDL; HDL; triglycerides; and combinations of these. In some embodiments, diagnostic results include data collected in the performance of a safety serum test, such as a safety serum test assessing a parameter selected from the group consisting of: C-reactive protein; amylase; lipase; AST; ALT; total bilirubin; and combinations of these.

Diagnostic results can include data collected in the performance of a serum marker assessment. The serum marker assessment can be performed with the patient in a fed or fasted state. The serum marker test diagnostic results can include an assessment of their changes over time. The serum marker diagnostic results can be used to assess adverse effects of a tissue treatment, such as the tissue treatment performed in the first clinical procedure. The serum marker test diagnostic results can represent a measurement of a compound selected from the group consisting of: amylase; lipase; glucose, insulin, C-peptide, C-reactive protein, creatine kinase, lactate; and combinations of these. In some embodiments, energy delivered in the second clinical procedure is decreased (e.g. decrease in power level, duration of energy delivered and/or temperature achieved), due to the assessment of an adverse effect represented in the serum marker diagnostic results.

Diagnostic results can include data collected in the performance of a tissue biopsy, such as an intestinal or other tissue biopsy followed by a histological evaluation of the biopsied tissue. These biopsy-based diagnostic results can include an assessment of a parameter selected from the group consisting of: depth of viability staining; enteroendocrine cell population; GIP-producing cell population; GLP-1 producing cell population; glucagon-producing cell quantity; surface topology of the duodenal mucosa; presence, absence, or substantial reduction in depth of plicae circulares; and combinations of these. One or more biopsies can be performed before the first clinical procedure, during the first clinical procedure; after the first clinical procedure, and/or thereafter. The diagnostic results can include a comparison between a first biopsy and a second biopsy. Biopsied tissue can include tissue proximal or distal to treated tissue. In some embodiments, tissue treated in the second clinical procedure is selected based on biopsy-based diagnostic results.

Diagnostic results can include data collected in a visualization procedure such as an endoscopic visualization procedure. Visualization procedures can be performed to assess a pattern of intestinal healing, such as when a pattern of intestinal healing is performed on tissue treated in a first clinical procedure to determine which tissue should be treated in a second clinical procedure. In some embodiments, tissue treated in a first clinical procedure is visually examined in a subsequent clinical procedure, and tissue which has retained prominent plicae circulares is selected for a second treatment.

Diagnostic results can include data collected in a patient weight measurement procedure. Tissue treatment performed in the second clinical procedure can be modified or otherwise configured based on weight-related diagnostic results, such as a change in weight between a time before the first clinical procedure is performed and a time after the first clinical procedure is performed. In some embodiments, insufficient weight loss during that time period causes additional tissue to be treated in the second clinical procedure, such as additional gastric mucosal and/or ileal mucosal tissue, such as when no gastric mucosal and/or ileal mucosal tissue is treated in the first clinical procedure.

Diagnostic results can include data collected in a cholesterol parameter measurement test. Tissue treatment performed in the second clinical procedure can be modified or otherwise configured based on cholesterol-related diagnostic results, such as a change in one or more cholesterol parameters between a time before the first clinical procedure is performed and a time after the first clinical procedure is performed. In some embodiments, insufficient improvement in one or more cholesterol parameters during that time period causes additional tissue to be treated in the second clinical procedure, such as additional gastric mucosal and/or ileal mucosal tissue, such as when no gastric mucosal and/or ileal mucosal tissue is treated in the first clinical procedure.

Diagnostic results can include an assessment of tissue treatment depth, such as a depth of ablation measurement that is determined using a viability staining procedure. In some embodiments, one or more energy delivery parameters used in the second clinical procedure are modified or otherwise configured based on the results of assessing the tissue treatment depth achieved in one or more energy deliveries performed in the first clinical procedure.

Diagnostic results can include data collected in the performance of a procedure to assess mucosal regrowth. One or more second clinical procedure parameters are modified or otherwise configured based on a parameter selected from the group consisting of: amount of mucosal regrowth; type of mucosal regrowth; mucosal regrowth pattern or geometry; continuity of mucosal regrowth; quality of mucosal regrowth (i.e., presence or absence of fully reconstituted villous structures); and combinations of these. One or more tissue portions are selected for treatment in the second clinical procedure based on the mucosal regrowth-based diagnostic results. In some embodiments, a larger portion (e.g. a longer length of GI tissue, more circumferential portion of GI tissue and/or deeper depth of tissue) of tissue is treated if the mucosal growth rate is above a threshold. Correspondingly, a smaller portion of tissue may be treated if the mucosal growth rate is below a threshold. In some embodiments, diagnostic results representing discontinuous or "patch-like" regrowth can drive the elapsed time between the first clinical procedure and the second clinical procedure to be shorter in duration, such as a reduction to an elapsed time comprising between 3 and 7 days.

Diagnostic results can include data collected during a procedure assessing tissue expansion, such as a procedure assessing submucosal tissue expansion. Data collected can include data representing one or more of: area of expansion; depth of expansion; safety of expansion and effectiveness of expansion.

As described above, additional clinical procedures (e.g. a third, a fourth, etc) can be performed after the second clinical procedure of STEP 560, using similar or dissimilar systems, devices and methods to either the first clinical procedures or the second clinical procedure. Diagnostic results as described hereabove can be collected during and/or between the additional clinical procedures, and the additional clinical procedures can be modified or otherwise configured based on one or more analyses of the diagnostic results.

Referring now to FIG. 3, a side sectional view of the distal portion of a treatment device inserted into a curvilinear section of duodenum is illustrated, consistent with the present inventive concepts. Treatment device 100 comprises shaft 110, a relatively flexible, biocompatible, elongate structure configured for insertion into a body lumen such as the duodenal lumen shown. Shaft 110 is typically connected to a handle on its proximal end, not shown but configured to allow an operator to advance, retract and otherwise manipulate or control ablation device 100. Ablation device 100 can be configured for delivery over a guidewire, via a lumen from a proximal portion to a distal portion, or via a rapid exchange sidecar in the distal portion of the device (guidewire lumen and sidecar not shown but known to those of skill in the art). Shaft 110 is shown inserted through introducer 50 which can comprise an endoscope, sheath, or other body introduction device.

Treatment device 100 further comprises treatment assembly 140, which can be similar to treatment assembly 140 of FIG. 1. Treatment assembly 140 can be expandable and/or it can include one or more expandable elements. Treatment assembly 140 comprises treatment element 145, which is constructed and arranged to treat target tissue. Treatment element 145 can comprise one or more treatment elements such as a balloon configured to receive sufficiently hot or cold ablative fluid; a fluid delivery element such as a nozzle configured to deliver ablative fluid directly onto tissue; one or more electrodes configured to deliver RF energy to tissue; and/or other ablation or other tissue treatment elements such as those described in reference to FIG. 1 hereabove.

Treatment assembly 140 has been positioned in a distal portion of duodenal tissue, such as a section that includes an expanded segment of submucosal tissue (expansion not shown). Treatment assembly 140 has been radially expanded such as to contact the mucosal surface of the duodenum at a $1^{st}$ target tissue or treatment portion, which is distal to a series of target tissue or treatment portions comprising sequential target tissue portions 2 through 6 as shown in FIG. 3. Treatment element 145 is positioned to ablate or otherwise treat the $1^{st}$ target tissue portion. Treatment element 145 can be operably connected to one or more wires, fluid delivery tubes, or other conduits, not shown but such as conduit 141 of FIG. 1, such that treatment element 145 can treat tissue proximate to treatment element 145.

Treatment assembly 140 is sized to allow positioning in the curved segments of a gastrointestinal segment such as a curved segment of the duodenum, such that treatment assembly 140 can be expanded without exerting undesired force onto tissue (e.g. expanded to contact the tissue wall and/or to position treatment element 145 a fixed distance from the tissue wall). In some embodiments, treatment assembly 140 comprises a length less than or equal to 30 mm, such as less than or equal to 25 mm, less than or equal to 20 mm or less than or equal to 15 mm After treatment of the $1^{st}$ target tissue portion, treatment assembly 140 can be repositioned to the $2^{nd}$ target tissue portion, just proximal to the $1^{st}$ target tissue portion, with or without contracting treatment assembly 140 prior to the repositioning. Subsequently, a second tissue treatment (e.g. a second energy delivery) can be performed. The steps of repositioning and treating portions of target tissue are repeated until target tissue portions 3, 4, 5 and 6 have been treated. In a single clinical procedure, the combined length of target tissue portions 1 through 6 typically represent between 25% and 100% of the length of the duodenal mucosa length. Alternatively or additionally, other tissue can be treated, such as has been described hereabove.

Target tissue portions 1 through 6 typically include common or overlapping tissue portions, such as is shown in FIG. 3. While the embodiment of FIG. 3 shows six target tissue portions being treated, more or fewer segments can be treated. Tissue treatments can be performed in a contiguous manner (e.g. $1^{st}$ portion followed by $2^{nd}$ portion, followed by $3^{rd}$ portion, etc); however any order can be performed. In some embodiments, multiple contiguous or discontiguous tissue portions are treated simultaneously. In some embodiments, contiguous tissue portions are treated by device 100 continuously, as treatment assembly 140 is translated proximally and/or distally, such as via a manual or automated retraction and/or advancement, respectively, as has been described in reference to FIG. 1 hereabove. In some embodiments, treatment of target tissue is performed as treatment assembly 140 translates at a rate of at least 10 cm per minute.

Referring now to FIG. 4, a flow chart of a method for treating a patient comprising monitoring a tissue treatment procedure is illustrated, consistent with the present inventive concepts. In STEP 610, a tissue treatment procedure on a patient is initiated. The tissue treatment procedure can be performed using system 10 of FIG. 1 and/or device 100 of FIG. 3. The tissue treatment procedure can be similar to the first or second clinical procedures of STEPS 530 and 560, respectively, or FIG. 2. The tissue treatment can be performed to provide a therapeutic benefit to a patient, such as a patient with a disease or disorder selected from the group consisting of: diabetes; obesity; insulin resistance; a metabolic disorder and/or disease; and combinations of these.

In STEP 620, the tissue treatment procedure continues while being monitored, such as by one or more diagnostic tools such as those described in reference to FIG. 2 hereabove, or by a device or sensor of a tissue treatment system, such as by one or more sensors of system 10 of FIG. 1.

In STEP 630, an algorithm is configured to determine if a complication (e.g. a patient adverse event, a system or device failure or error, etc.) has occurred. Detectable complications include but are not limited to: patient bleeding; patient discomfort; pancreatic injury; intestinal perforation; unintended duodenal mechanical damage, such as unintended abrasion; excess thermal dose delivery; excess mucosal interface temperature; and combinations of these. In some embodiments, a pre-determined procedural time limit is included, and a complication results if the procedural time exceeds that limit.

If a complication is detected, STEP 640 is performed. If a complication is not detected, STEP 650 is performed.

In STEP 640, an algorithm is configured to determine whether the tissue treatment procedure should be stopped. If the complication is sufficient to stop the procedure, the procedure is stopped in STEP 660. If the procedure should be continued, monitoring and tissue treatment continues in STEP 620. In some embodiments, the algorithm of STEP 640 is further configured to determine if one or more system, device and/or method configuration parameters should be modified prior to continuing tissue treatment and monitoring in STEP 620. Modifications can include treatment of a different tissue portion, a change to an energy delivery parameter and/or a change to one or more other configuration parameters described in detail in reference to FIGS. 1 through 3 hereabove. The system and/or one or more tissue treatment devices can be configured to be automatically modified, or to be manually modified such as by a clinician or other operator of the system that is presented modification information by the algorithm of STEP 640.

In STEP 650, an algorithm is configured to determine if the tissue treatment procedure is complete. The algorithm can comprise a manual assessment by an operator of the system, or it may be semi-automated or fully automated. If it is determined that complete tissue treatment has been achieved, the procedure is stopped in STEP 660. If tissue treatment should continue, treatment and monitoring is continued in STEP 620.

Procedures that are stopped due to one or more complications, such as can be detected in STEP 630, can result in the performance of an additional clinical procedure, such as a clinical procedure performed at least twenty-four hours after the complication has been detected, such as the second clinical procedure described in reference to FIG. 2 hereabove.

While the preferred embodiments of the devices and methods have been described in reference to the environment in which they were developed, they are merely illustrative of the principles of the inventions. Modification or combinations of the above-described assemblies, other embodiments, configurations, and methods for carrying out the invention, and variations of aspects of the invention that are obvious to those of skill in the art are intended to be within the scope of the claims. In addition, where this application has listed the steps of a method or procedure in a specific order, it may be possible, or even expedient in certain circumstances, to change the order in which some steps are performed, and it is intended that the particular steps of the method or procedure claim set forth herebelow not be construed as being order-specific unless such order specificity is expressly stated in the claim.

What is claimed is:

1. A method for treating a patient comprising:
    selecting a patient diagnosed with diabetes;
    performing a first treatment comprising ablating a first tissue portion having a first length in a first axial segment of the patient's duodenum with heat;
    performing a diagnostic procedure comprising assessing a pattern of mucosal regrowth on the first tissue portion after performing the first treatment, wherein said diagnostic procedure produces a diagnostic result;
    determining a mucosal regrowth rate based upon the diagnostic result;
    comparing the determined mucosal regrowth rate with a threshold mucosal regrowth rate;
    selecting a second axial segment of the patient's duodenum different from the first axial segment of the duodenum; and
    performing a second treatment on the second tissue portion of the patient's duodenum;
    wherein a length of the second portion is longer than the length of the first tissue portion when the determined mucosal regrowth rate is greater than the threshold mucosal regrowth rate.

2. The method according to claim 1, wherein the first treatment comprises delivery of thermal energy from a balloon filled with fluid at an ablative temperature.

3. The method according to claim 1, wherein the second treatment comprises a non-ablation treatment selected from the group consisting of mechanical removal of mucosal tissue, sclerosant injection into the submucosa, radioactive seed deposition, chemical spray, an acid spray, drug delivery via an agent-eluting balloon, and combinations of these.

4. The method according to claim 1, further comprising implanting a device in at least a portion of the duodenum.

5. The method according to claim 4 further comprising removing at least a portion of the implanted device.

6. The method according to claim 1, wherein the patient receives an improved therapeutic benefit after the second treatment is performed.

7. The method according to claim 1, wherein the second treatment is performed at least 6 months after the first treatment is performed.

8. The method according to claim 1, wherein the second treatment is performed at least 1 year after the first treatment is performed.

9. The method according to claim 1, wherein the second treatment is performed after a time period has elapsed since the first procedure, and wherein the time period duration is determined prior to the performance of the first procedure.

10. The method according to claim 1, further comprising expanding one or more layers of duodenal tissue.

11. The method according to claim 1, wherein the first tissue portion comprises approximately 67% or less of the duodenal mucosa.

12. The method according to claim 1, wherein the first tissue portion comprises a volume of tissue below a threshold, and wherein the threshold is selected to prevent the occurrence of an adverse event.

13. The method according to claim 12, wherein the second tissue portion comprises a larger volume of tissue than the volume of tissue of the first tissue portion.

14. The method according to claim 12, wherein the threshold is selected to prevent or reduce hypoglycemia.

15. The method according to claim 1, wherein the second tissue portion is located at an anatomical location different from that of the first tissue portion.

16. The method according to claim 1, wherein the second tissue portion further comprises at least one of a tissue volume which differs from that of the first tissue portion and a circumferential segment of a duodenum which differs from that of the first tissue portion.

17. The method according to claim 16, wherein the second tissue portion comprises a tissue volume different from that of the first tissue portion.

18. The method according to claim 16, wherein the second tissue portion comprises a circumferential segment of duodenum different from that of the first tissue portion.

19. The method according to claim 1, wherein the diagnostic procedure measures a level of HOMA-IR.

20. The method according to claim 1, wherein the diagnostic procedure measures a level of ALT.

21. The method according to claim 1, wherein the second treatment comprises an ablative treatment.

22. The method according to claim 1, wherein the second portion of the patient's tissue treated in the second treatment comprises a length of tissue shorter than a length of the first tissue portion of the patient's tissue when the determined mucosal regrowth rate is below a threshold mucosal regrowth rate.

23. The method according to claim 1, wherein determining a mucosal regrowth rate comprise an assessing continuity of mucosal regrowth.

24. The method according to claim 1, wherein assessing continuity of mucosal regrowth comprises assessing the presence of fully reconstituted villous structures.

25. The method according to claim 1, wherein the pattern of mucosal regrowth is assessed from 3 to 7 days after the first treatment is performed.

26. The method according to claim 1, further comprising selecting a second treatment parameter for use in the second treatment different than a first treatment parameter used in the first treatment based upon the diagnostic result.

* * * * *